United States Patent
Inana

(10) Patent No.: US 7,442,341 B2
(45) Date of Patent: Oct. 28, 2008

(54) CARTRIDGE RETAINING MECHANISM FOR NUCLEIC ACID EXTRACTING APPARATUS

(75) Inventor: Katsuya Inana, Asaka (JP)

(73) Assignee: Fujifilm Corporation, Tokyo (JP)

( * ) Notice: Subject to any disclaimer, the term of this patent is extended or adjusted under 35 U.S.C. 154(b) by 330 days.

(21) Appl. No.: 11/355,990

(22) Filed: Feb. 17, 2006

(65) Prior Publication Data

US 2006/0186037 A1    Aug. 24, 2006

(30) Foreign Application Priority Data

Feb. 21, 2005    (JP)    ............ P. 2005-043965

(51) Int. Cl.
*B01L 11/00*    (2006.01)
*B01L 9/00*    (2006.01)
*G01N 1/18*    (2006.01)

(52) U.S. Cl. .................. 422/101; 422/104; 436/178

(58) Field of Classification Search .......... 422/101, 422/102, 104; 435/6, 287.2; 436/177, 178
See application file for complete search history.

(56) References Cited

U.S. PATENT DOCUMENTS 5,114,858 A * 5/1992 Williams et al. ........... 435/270
5,436,328 A * 7/1995 Malmquist .............. 536/25.42
6,110,428 A * 8/2000 Borst et al. ................ 422/101

FOREIGN PATENT DOCUMENTS

JP    2005-328730 A    12/2005

* cited by examiner

*Primary Examiner*—Anh T. N. Vo
(74) *Attorney, Agent, or Firm*—Birch, Stewart, Kolasch & Birch, LLP

(57) ABSTRACT

A cartridge retaining mechanism equipped in a nucleic acid extracting apparatus for extracting a nucleic acid, the mechanism comprising: a cartridge that comprises: a cartridge main body that has a cylindrical shape with a bottom, and the bottom is shaped in a funnel shape; a nucleic acid-adsorbing solid carrier that traps a nucleic acid, and the carrier is disposed at the bottom; and a cartridge cap that is detachably mounted on an open end of the cartridge main body, a supporting part that supports the cartridge; and a pressure-proof retaining part that pushes the cartridge cap, wherein a cylindrical rib with a diameter smaller than a diameter of the cartridge main body is formed on an upper plane of the cartridge cap so that the cylindrical rib protrudes from the upper plane; a nozzle-receiving opening to which a pressure nozzle is pressed is formed at the cylindrical rib; and an aperture through which the cylindrical rib is inserted is formed in the pressure-proof retaining part, and wherein when the pressure nozzle is pressed to the nozzle-receiving opening, along with the nozzle-receiving opening being exposed from the aperture, the cartridge cap is pressed by the pressure-proof retaining part and simultaneously the cartridge main body is supported by the supporting part.

4 Claims, 4 Drawing Sheets

CARTRIDGE RETAINING MECHANISM FOR NUCLEIC ACID EXTRACTING APPARATUS

BACKGROUND OF THE INVENTION

1. Field of the Invention

The present invention relates to a mechanism for retaining a cartridge for extracting a nucleic acid to be equipped in a nucleic acid extracting apparatus which automatically extracts a nucleic acid from a sample solution containing the nucleic acid.

2. Description of the Related Art

At present, an automatic nucleic acid extracting system automatically extracting DNA and RNA is being proposed for post-genome researches (for example, Japanese Patent Application Publication No. 2005-328730).

FIG. 4 is an illustration showing the outline of an automatic nucleic acid extracting system.

The automatic nucleic acid extracting system 100 has a cartridge holder 103 retaining plural cartridges 104 in an aligned state, a pressure nozzle 101 for feeding pressurized air to the cartridges 104, and a moving head 102 retaining the pressure nozzle 101 and being capable of moving in the aligned direction of the cartridges 104. Further, in the automatic nucleic acid extracting system 100, recovering containers 106, which recovers the recovering solution discharged from the cartridges 104 in a recovering step of recovering a nucleic acid that has been once adsorbed on an adsorbing medium provided in the cartridges 104 through a recovering solution and a rack 105 retaining the recovering containers 106 are provided.

In such an automatic nucleic acid extracting system 100, after injecting a sample solution containing a nucleic acid or a solution such as a rinsing solution and a recovering solution, into the cartridge 104 from an injecting nozzle, the pressure nozzle 101 is pressed onto an open end of the cartridge 104 to feed pressurized air to the interior of the cartridge 104 from the pressure nozzle 101, whereby the solution is passed through the adsorbing medium and discharged from the cartridge 104 to the recovering container 106 or a waste liquor container, which is not shown in the drawing.

SUMMARY OF THE INVENTION

Meanwhile, with respect to the nucleic acid extracting system 100 shown in FIG. 4 having such a constitution that, upon injecting the recovering solution, the pressure nozzle 101 is pressed onto an air inlet opening of the cartridge 104 from above, and a cap, which is not shown in the figure, is mounted on the air inlet opening, so as to pressurize and seal the interior of the cartridge 104, there has conventionally been a demand of increasing the amount of the processed solution by increasing the area of the filter. Accordingly, expansion of the cross sectional area of the cartridge 104 compared with the conventional area is under study.

On the other hand, in the aforementioned conventional constitution, when the diameter d of the cartridge 104 is increased accompanied with the increase of the cross sectional area of the cartridge 104, the pressurizing force applied to the cap of the cartridge 104 upon pressurizing and sealing is also increased in proportion to the expansion of the cross sectional area, and therefore it becomes necessary to change the structure of the apparatus so as to increase the strength thereof.

In the case of the constitution as shown in FIG. 5, in which, with use of a rubber-made pressure nozzle 101, upon extracting a nucleic acid from a filter F, the pressure nozzle 101 is pressed onto the air inlet opening of the cartridge 104 to feed air there into, the pressure nozzle 101 receives a rising force $R = P \times S$ in the direction opposite to the pressing direction thereof, with the assumption that A represents the pressing force with which the pressure nozzle 101 is pressed onto the air inlet opening, P represents the pressure of the air, and S represents the cross sectional area of the cartridge 104.

In order to ensure airtightness of the interior of the cartridge 104, it has been necessary to make the pressing force A of the pressure nozzle 101 larger than the rising force R, and thus make the pressing force A must necessarily larger with the increase of the cross sectional area S of the cartridge 104. For example, in the case where the cross sectional area S is increased by 10 times, the force R applied to the pressure nozzle 101 is $P \times 10 \times S$, and thus the pressing force A should be increased by 10 times. In order to cope with the increased pressing force A only by the constitution of the apparatus, there is such a concern that the pressing mechanism and the driving mechanism of the apparatus must be modified drastically.

In such a manner, there has been such a demand that a cartridge 104 having a larger diameter is used while maintaining airtightness of the cartridge, without drastic modification of the constitution of the apparatus.

The invention has been made under the aforementioned circumstances, and the object thereof is to provide such a cartridge retaining mechanism for a nucleic acid extracting apparatus that can retain airtightness upon pressurizing, without drastic modification of the constitution of the nucleic acid extracting apparatus.

The aforementioned object of the invention is attained by the following (1) to (4).

(1) A cartridge retaining mechanism equipped in a nucleic acid extracting apparatus for extracting a nucleic acid, the cartridge retaining mechanism comprising:
   a cartridge that comprises:
   a cartridge main body that has a cylindrical shape with a bottom, and the bottom is shaped in a funnel shape;
   a nucleic acid-adsorbing solid carrier that traps a nucleic acid, and the nucleic acid-adsorbing solid carrier is disposed at the bottom of the cartridge main body; and
   a cartridge cap that is detachably mounted on an open end of the cartridge main body,
   a supporting part that supports the cartridge; and
   a pressure-proof retaining part that pushes the cartridge cap,
   wherein a cylindrical rib with a diameter smaller than a diameter of the cartridge main body is formed on an upper plane of the cartridge cap so that the cylindrical rib protrudes from the upper plane;
   a nozzle-receiving opening to which a pressure nozzle is pressed is formed at the cylindrical rib; and
   an aperture through which the cylindrical rib is inserted is formed in the pressure-proof retaining part, and
   wherein when the pressure nozzle is pressed to the nozzle-receiving opening, along with the nozzle-receiving opening being exposed from the aperture, the cartridge cap is pressed by the pressure-proof retaining part and simultaneously the cartridge main body is supported by the supporting part.

(2) The cartridge retaining mechanism as described in (1) above,
   wherein the cartridge cap has a configuration to be fitted to the cartridge main body.

(3) The cartridge retaining mechanism as described in (2) above,
   wherein the cartridge cap has a fitting protrusion and the cartridge main body has a fitting groove.

(4) The cartridge retaining mechanism as described in (2) above, wherein the cartridge cap has a fitting groove and the cartridge main body has a fitting protrusion.

According to the cartridge retaining mechanism associated with the invention, a cartridge cap is attached to an open end of a cartridge main body, and the interior of the cartridge main body can be maintained airtight by pressing a pressure nozzle onto a nozzle-receiving opening formed at the cylindrical rib of the cartridge cap. Further, the constitution of the mechanism is such that along with the cartridge cap being pressed against a pressure-proof retaining part, the cartridge main body is supported by the supporting part. Then, even if the pressure of the interior of the cartridge main body rises due to pressurized air fed from the pressure nozzle into the interior of the cartridge main body during the extraction of a nucleic acid, the pressure directly applied to the pressure nozzle is suppressed since the pressure is received by the cartridge cap pressed by the pressure-proof retaining part. And airtightness of the interior of the cartridge can be ensured without release of the pressure nozzle from the nozzle-receiving opening. In such a constitution, accordingly, the pressure from the interior of the cartridge applied to the pressure nozzle during application of the pressure increased by the expansion of the cartridge diameter is received by the cartridge cap and the pressure-proof retaining part, whereby there is no necessity of modifying the mechanism of pressing the pressure nozzle onto the cartridge in the nucleic acid extracting apparatus, since it is possible to adopt the same diameter of the nozzle-receiving opening formed in the cartridge cap as that of the conventional one, even if the diameter of the cartridge main body is increased as a result of increasing the area of the nucleic acid adsorbing solid carrier.

In the aforementioned cartridge retaining mechanism, it is preferred that a fitting part that fits to the cartridge main body is formed in the cartridge cap. With such a configuration, airtightness can be further surely ensured since, during the feeding of pressurized air, leakage of the pressurized air caused by the formation of a gap between the cartridge main body and the cartridge cap can be prevented.

DETAILED DESCRIPTION OF THE INVENTION

In the following, some practical embodiments of the invention are described in detail based on drawings.

Figure 1:
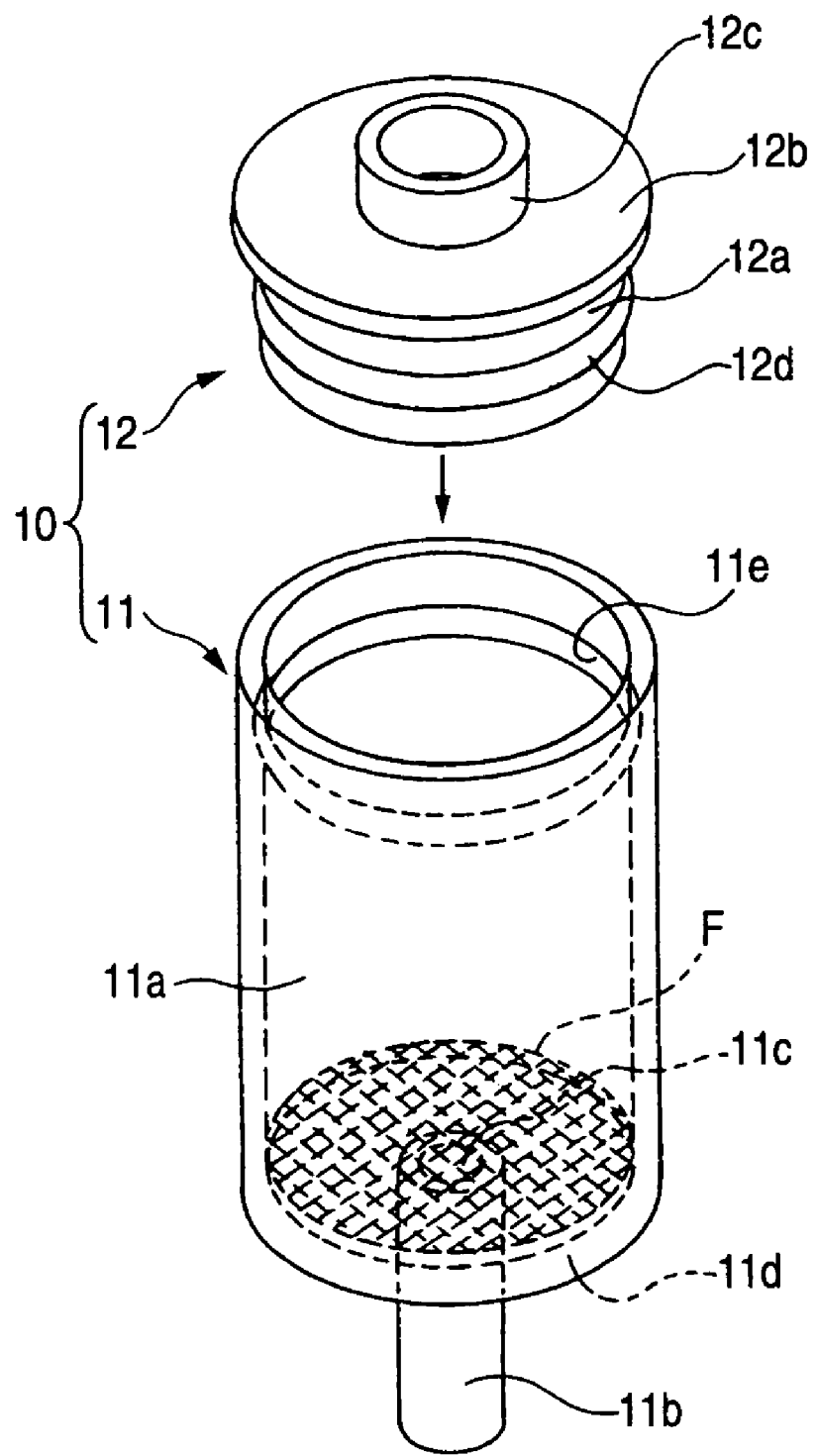
FIG. 1 is an exploded perspective view showing a cartridge used for a cartridge retaining mechanism associated with the invention.
Figure 2:
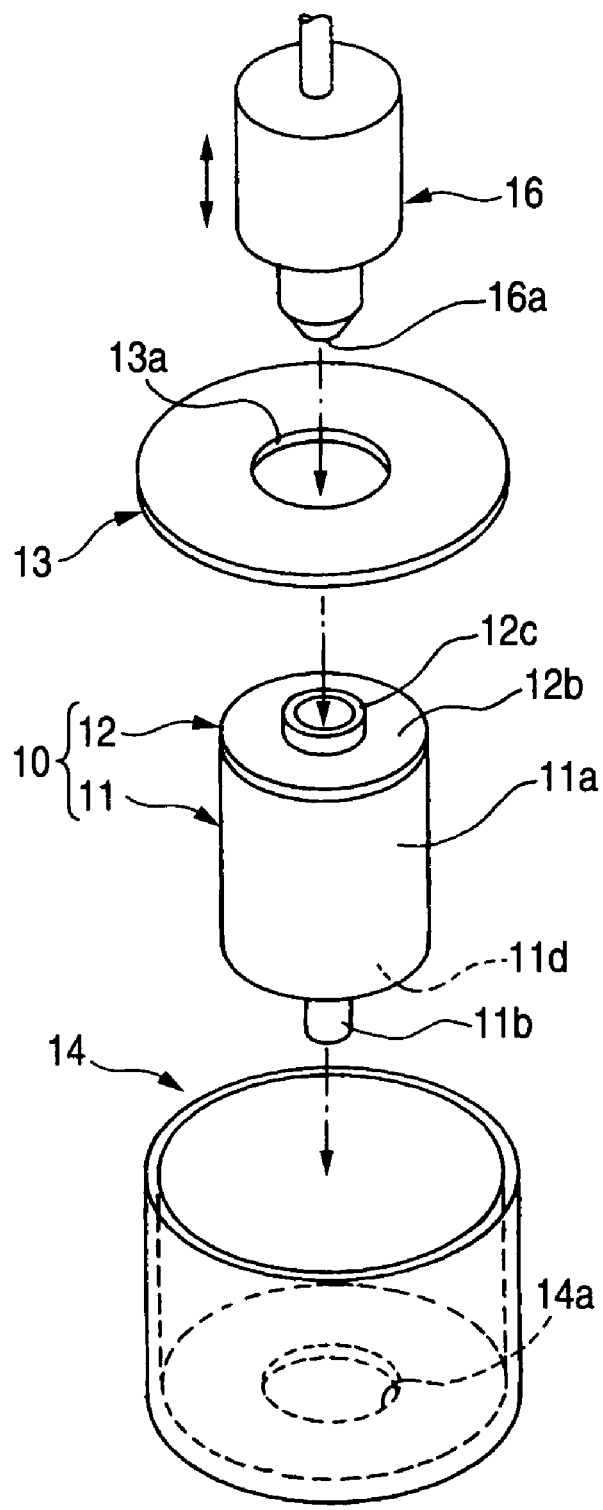
FIG. 2 is an exploded perspective view showing a cartridge retaining mechanism associated with the invention.
Figure 3:
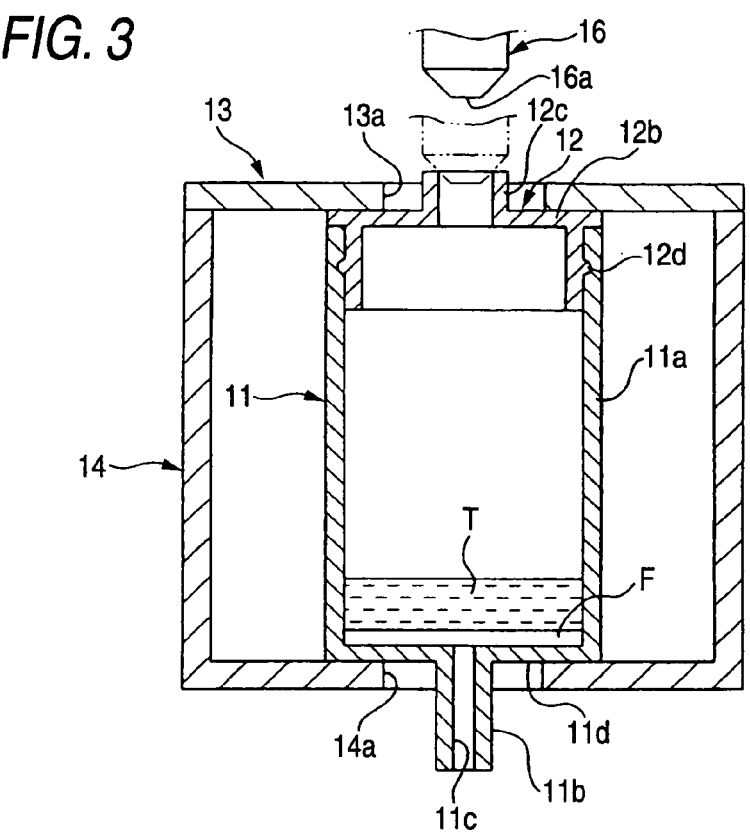
FIG. 3 is a cross-sectional view explaining the state of pressing a pressure nozzle to a cartridge retaining member.
Figure 4:
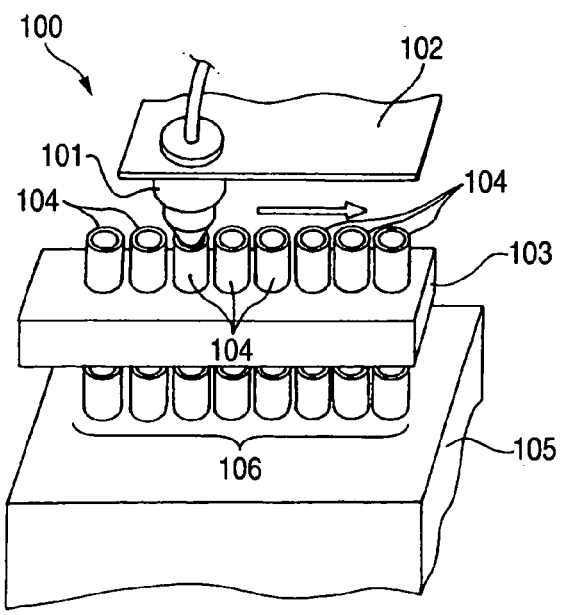
FIG. 4 is a drawing showing the outline of an automatic nucleic acid extracting system.
Figure 5:
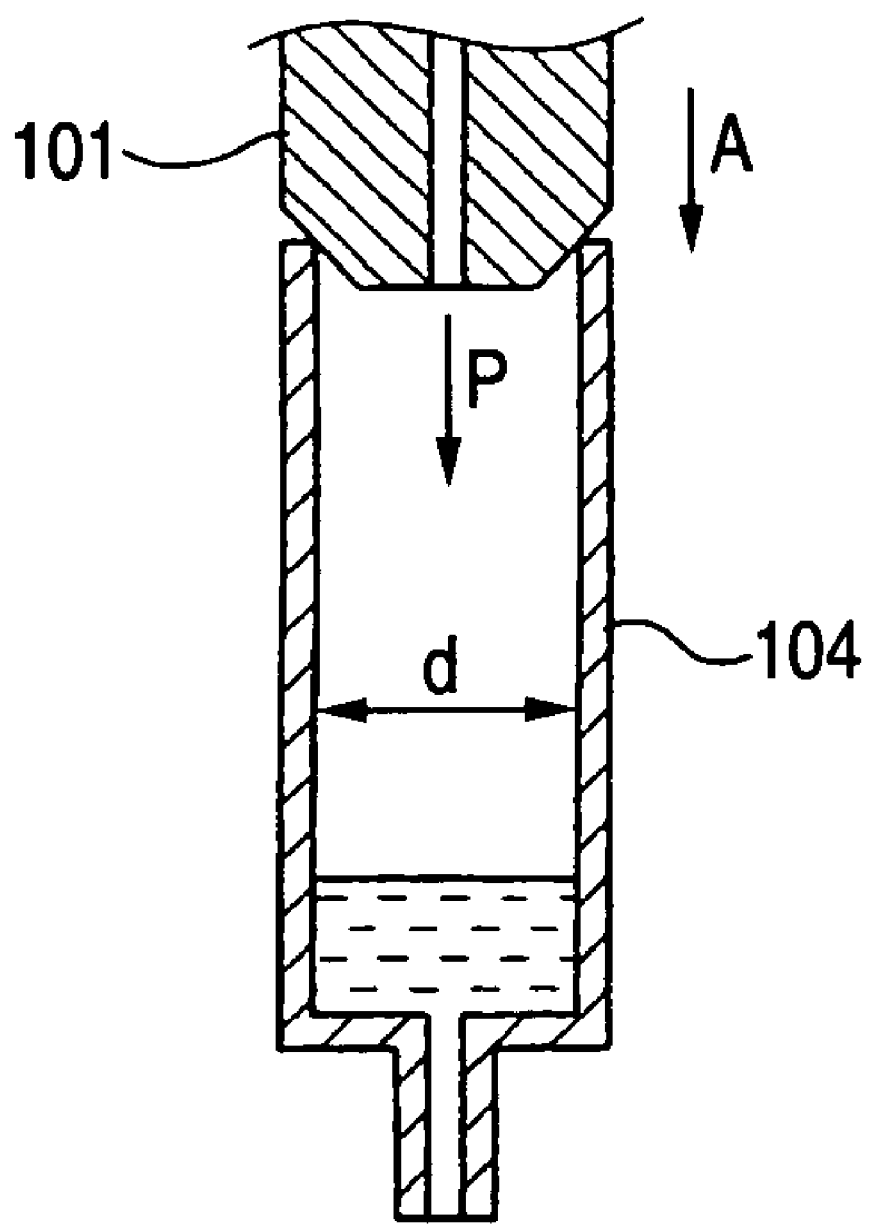
FIG. 5 is a drawing showing the state of feeding pressurized air to a cartridge.

FIG. 1 is an exploded perspective view showing a cartridge used for a cartridge retaining mechanism associated with the invention. FIG. 2 is an exploded perspective view showing a cartridge retaining mechanism associated with the invention. FIG. 3 is a cross-sectional view showing the cartridge retaining mechanism.

The cartridge retaining member associated with the invention is equipped in a nucleic acid extracting apparatus. The nucleic acid extracting apparatus carries out the following step sequentially, i.e., (1) a step of passing a sample solution containing a nucleic acid through a nucleic acid-adsorbing porous membrane disposed in a cartridge to adsorb the nucleic acid in the nucleic acid-adsorbing porous membrane, (2) a step of rinsing the nucleic acid-adsorbing membrane having the nucleic acid adsorbed therein, and (3) a step of passing a recovering solution through the nucleic acid-adsorbing porous membrane to release the nucleic acid from the nucleic acid-adsorbing membrane and to recover the nucleic acid.

After the sample solution, the rinsing solution and the recovering solution (which will be generically referred to as a solution) are injected into the cartridge with an injecting nozzle, pressurized air is fed into the cartridge with a pressure nozzle, whereby the solution is discharged from the cartridge to a recovering container or the like. The cartridge retaining mechanism has such a function that it retains the cartridge when pressurized air is fed from the pressure nozzle to the cartridge.

As shown in FIG. 1, the cartridge 10 used for a cartridge retaining mechanism has a cartridge main body 11 which has an open upper and is of cylindrical shape with a bottom, the bottom being formed in funnel shape at the lower end. The cartridge main body 11 has a cylindrical body 11a and a discharging part 11b having a thin tube nozzle shape extending from the center of the end surface of the bottom of the cylindrical body 11a to the exterior. In the inner side of the discharging part 11b, a discharging opening 11c extending from the interior of the cartridge main body 11 to the exterior is opened.

A nucleic acid-adsorbing porous membrane F is retained at the bottom 11d of the cylindrical body 11a of the cartridge main body 11. The nucleic acid-adsorbing porous membrane F will be described later in detail.

In addition, the cartridge 10 has a cartridge cap 12 attached to the open end of the cylindrical body 11a of the cartridge main body 11. The cartridge cap 12 has a cylindrical inserting part 12a having an outer diameter substantially equal to the inner diameter of the cylindrical body 11a of the cartridge main body 11, a ceiling board 12b with a diameter expanded in a flange shape at the upper end of the inserting part 12a, and a cylindrical rib 12c arranged so as to protrude substantially from the center of the upper plane of the ceiling board 12b.

In the cylindrical rib 12c, a nozzle-receiving opening is formed extending from the lower end of the inserting part 12d of the cartridge cap 12 to the upper plane of the ceiling board 12b along the axial direction.

Further, on the outer peripheral plane of the inserting part 12a of the cartridge cap 12 is disposed a fitting protrusion 12d convexly provided along the peripheral direction. On the other hand, a fitting groove 11e is disposed on the inner peripheral plane at the upper end of the cylindrical body 11a of the cartridge main body 11. When the cartridge cap 12 is attached to the cartridge main body 11, the inserting part 12a of the cartridge cap 12 is inserted into the interior of the cylindrical body 11a of the cartridge main body 11, whereby the fitting protrusion 12d of the inserting part 12a is fitted into the fitting groove 11e of the cylindrical body 11a to fix the cartridge cap 12 to the cartridge main body 11.

As shown in FIG. 2, the cartridge 10 connecting the cartridge main body 11 and the cartridge cap 12 is accommodated in and supported by a supporting part 14. The supporting part 14, which is configured substantially in a receptacle-like shape, has, in its bottom plane, an inserting opening 14a to guide the discharge part 11b of the cartridge main body 11 to the exterior of the supporting part 14. The upper end of the supporting part 14 is left open, through which the cartridge 10 is mounted.

To the supporting part 14 into which the cartridge 10 is mounted, a pressure-proof retaining part 13 is attached from above. The pressure-proof retaining part 13, which is a disc-shaped member with a diameter substantially equal to the outer diameter of the supporting part 14, is brought into contact with the upper end of the supporting part 14 for fixation. The supporting part 14 may be fixed to, for example, the nucleic acid extracting apparatus side. In addition, at the center of the pressure-proof retaining part 13, an aperture 13a through which the nozzle tip 16a of the pressure nozzle 16 is inserted is formed.

FIG. 3 shows the state where the cartridge 11 is retained with the supporting part 14 and the pressure-proof retaining part 13 and the pressure nozzle 16 is being pressed. Under this state, along with the insertion of the discharge part 11b of the cartridge main body 11 into the inserting opening 14a, the bottom part 11d is brought into contact with and supported by the bottom of the supporting part 14. Further, along with the cylindrical rib 12c of the cartridge cap 12 being exposed towards the upper direction from the aperture 13a of the cartridge cap 12 attached to the open end of the cylindrical body 11a of the cartridge main body 11, the upper plane of the ceiling board 12b of the cartridge cap 12 is pressed against and retained by the lower plane of the pressure-proof retaining part 13. In such a manner, the cartridge 10 is retained in a state pressed both from above and below between the supporting part 14 and the pressure-proof retaining part 13. Upon pressurized air feeding, the pressure nozzle 16 descends from above the pressure-proof retaining part 13, and the nozzle tip 16a is pressed against the nozzle-receiving opening of the cylindrical rib 12c, whereby pressurized air is fed into the interior of the cartridge main body 11 via the nozzle-receiving opening and a solution T is discharged from the discharge opening 11c.

In the cartridge retaining mechanism of the present embodiment, the cartridge cap 12 is attached to the open end of the cartridge main body 11, and the interior of the cartridge main body 11 is kept airtight by pressing the pressure nozzle 16 against the nozzle-receiving opening formed in the cylindrical rib 12c of the cartridge cap 12. Further, the mechanism is so constituted that, along with the cartridge cap 12 being pressed against the pressure-proof retaining part 13, the cartridge main body 11 is supported by the supporting part 14. Then, even if the pressure in the interior of the cartridge main body 11 rises due to pressurized air fed from the pressure nozzle 16 into the interior of the cartridge main body 11 during the extraction of a nucleic acid, the pressure directly applied to the pressure nozzle 16 is suppressed since the pressure is received by the cartridge cap 12 pressed against the pressure-proof retaining part 13. And airtightness of the interior of the cartridge 10 can be ensured without release of the pressure nozzle 16 from the nozzle-receiving opening. In such constitution, accordingly, the pressure from the interior of the cartridge 10 applied to the pressure nozzle during application of the pressure increased by the expansion of the diameter of the cartridge 10 is received by the cartridge cap 12 and the pressure-proof retaining part 13, whereby there is no necessity of modifying the mechanism of pressing the pressure nozzle 16 onto the cartridge 10 in the nucleic acid extracting apparatus, since it is possible to adopt the same diameter of the nozzle-receiving opening formed in the cartridge cap 12 as that of the conventional one, even if the diameter of the cartridge main body 11 is increased as a result of increasing the area of the nucleic acid adsorbing solid carrier F.

Since the aforementioned cartridge retaining mechanism has a constitution in which the fitting protrusion formed in the cartridge cap 12 fits to the fitting groove formed in the cartridge main body 11, leakage of the pressurized air caused by the formation of a gap between the cartridge main body 11 and the cartridge cap 12 can be prevented. Accordingly, airtightness can be ensured with further certainty.

By way of precaution, the invention is not limited to the aforementioned embodiment, but appropriate modifications and improvements are applicable thereto.

For example, the fitting configuration for fitting the cartridge cap 12 to the cartridge main body 11 is not limited to the one set forth in the above-described embodiment. As an example, a fitting groove may be provided in the cartridge cap 12 and a fitting protrusion may be provided in the cartridge main body 11.

Next, the nucleic acid-adsorbing porous membrane (nucleic acid-adsorbing porous material) equipped in the cartridge in the aforementioned embodiments will be described in detail.

The nucleic acid-adsorbing porous membrane incorporated in the cartridge is basically a porous material, through which a nucleic acid can be passed. The surface thereof has a function of adsorbing a nucleic acid in a sample solution through chemical bonding power, and retains adsorption upon rinsing with a rinsing solution but releases the nucleic acid upon recovering with a recovering solution by reducing the adsorbing power.

The aforementioned nucleic acid-adsorbing porous membrane incorporated in the nucleic acid extracting cartridge is characterized by such a porous membrane adsorbing a nucleic acid through an interaction that ionic bond substantially does not contribute to. This means that the porous membrane is not ionized under the using conditions for the porous membrane side, and it is anticipated that a nucleic acid and the porous membrane attract each other by changing the polarity of the environment. According to the constitution, a nucleic acid can be isolated and purified with excellent separation performance and good rinsing efficiency. In a preferred embodiment, the nucleic acid-adsorbing porous membrane is a porous membrane having a hydrophilic group, and in this case, it is anticipated that a nucleic acid and the hydrophilic group of the porous membrane attract each other by changing the polarity of the environment.

The porous membrane having a hydrophilic group means a porous membrane made of a material that has a hydrophilic group by itself, or a porous membrane having a hydrophilic group introduced thereto by treating or coating a material constituting the porous membrane. The material constituting the porous membrane may be either an organic material or an inorganic material. Examples thereof include a porous membrane made of an organic material having a hydrophilic group by itself, a porous membrane having a hydrophilic group introduced thereto by treating an organic material having no hydrophilic group, a porous membrane having a hydrophilic group introduced thereto by coating a porous membrane made of an organic material having no hydrophilic group with a material having a hydrophilic group, a porous membrane made of an inorganic material having a hydrophilic group by itself, a porous membrane having a hydrophilic group introduced thereto by treating an inorganic material having no hydrophilic group, and a porous membrane having a hydrophilic group introduced thereto by coating a porous membrane made of an inorganic material having no hydrophilic group with a material having a hydrophilic group. In consideration of the facility of processing, an organic material, such as an organic high polymer, is preferably used as a material for forming the porous membrane.

The hydrophilic group herein designates a polar group (atomic group) capable of exerting an interaction with water and includes all groups (atomic groups) that is capable of participating in the adsorption of a nucleic acid. The hydrophilic group is preferably a group having a moderate interaction with water (See the term "groups having less strong hydrophilicity" in article "hydrophilic group" in Kagaku Daijiten (Comprehensive Dictionary of Chemistry), published by Kyoritsu Shuppan Co., Ltd.). Examples thereof include a hydroxyl group, a carboxyl group, a cyano group, an oxyethylene group, an amino group and an amide group, and a preferred example thereof is a hydroxyl group.

As the examples of the porous membrane having a hydrophilic group that can be put into practice of the invention include a porous material made of an organic material having an amide group. As the organic material having an amide group, polyamide can be preferably used. Examples of the polyamide include fibroin, polyamino acid, polypeptide, polyacrylamide, nylon 46, nylon 66, nylon 610, nylon 612, nylon 6, nylon 7, nylon 11 and nylon 12, but the invention is not limited thereto. Modified nylon, such as N-methyl modified nylon, N-alkoxymethyl modified nylon and N-alkylthiomethyl modified nylon, can also be used. As regards the polyamide porous membrane, those obtained by using the materials and methods disclosed in U.S. Pat. Nos. 2,783,894, 3,408,315, 4,340,479, 4,340,480 and 4,450,126, German Patent No. 3,138,525, and JP-A-58-37842 can be used, but the invention is not limited thereto.

As the example of the porous membrane made of an organic group having a hydroxyl group that can be used in the invention, porous membranes made of polyhydroxyethyl acrylate, polyhydroxyethyl methacrylate, polyvinyl alcohol, polyvinylpyrrolidone, polyacrylic acid, polymethacrylic acid, polyoxyethylene, acetylcellulose, or a polysaccharide, such as a mixture of plural kinds of acetylcellulose having different acetyl values can be mentioned. And, in particular, a porous membrane of an organic material having a polysaccharide structure can be preferably used.

Moreover, as still other examples of the organic material for the porous membrane, a saponification product of a vinyl acylate polymer or a saponification product of a copolymer or two or more monomers containing at least a monomer unit of vinyl acylate can be preferably used. The saponification product of a vinyl acylate polymer or the saponification product of a copolymer or two or more monomers containing at least a monomer unit of vinyl acylate in an amount of 1% by mole or more with a degree of saponification of 1% or more is preferred, and the acyl group of the vinyl acylate is preferably at least one selected from an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group.

As the example of the aforementioned polysaccharide structure, cellulose, hemicellulose, dextran, agarose, dextrin, amylose, amylopectin, starch, glycogen, pullulan, mannan, glucomannan, lichenin, isolichenin, laminarin, carrageenan, xylan, fructan, alginic acid, hyaluronic acid, chondroitin, chitin and chitosan can be used. Moreover, examples thereof further include derivatives of the aforementioned polysaccharide structures, and in particular, ester derivatives are preferably used. The invention is not limited to the materials mentioned above, so long as the material is of any polysaccharide structure and any derivative thereof.

In addition, saponification products of the ester derivatives of the aforementioned polysaccharide structures may be more preferably used.

As the ester of the ester derivative of the aforementioned polysaccharide structure, those selected from at least one of a carboxylate ester, a nitrate ester, a sulfate ester, a sulfonate ester, a phosphate ester, a phosphonate ester and a pyrophosphate ester are preferred. Saponification products of one of the aforementioned polysaccharide structures having a carboxylate ester, a nitrate ester, a sulfate ester, a sulfonate ester, a phosphate ester, a phosphonate ester and a pyrophosphate ester can also be more preferably used.

As the carboxylate ester of one of the aforementioned polysaccharide structures, those selected from at least one of an alkylcarbonyl ester, an alkenylcarbonyl ester, an aromatic carbonyl ester and an aromatic alkylcarbonyl ester are preferred. Saponification products of one of the polysaccharide structures having an alkylcarbonyl ester, an alkenylcarbonyl ester, an aromatic carbonyl ester and an aromatic alkylcarbonyl ester can also be more preferably used.

As the ester group of the alkylcarbonyl ester of one of the aforementioned polysaccharide structures, those selected from at least one of an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group are preferred. Saponification products of one of the polysaccharide structures having an ester group selected from at least one of an acetyl group, a propyonyl group, a butyloyl group, a valeryl group, a heptanoyl group, an octanoyl group, a decanoyl group, a dodecanoyl group, a tridecanoyl group, a hexadecanoyl group and an octadecanoyl group can also be more preferably used.

The ester group of the alkenylcarbonyl ester of one of the aforementioned polysaccharide structures is preferably at least one selected from an acrylic group and a methacrylic group. Saponification products of one of the aforementioned polysaccharide structures having an ester group selected from an acrylic group and a methacrylic group can also be more preferably used.

The ester group of the aromatic carbonyl ester of one of the aforementioned polysaccharide structures is preferably at least one selected from a benzoyl group and a naphthaloyl group. Saponification products of one of the aforementioned polysaccharide structures having a benzoyl group and a naphthaloyl group can also be more preferably used.

As the nitrate ester of one of the aforementioned polysaccharide structures, nitrocellulose, nitrohemicellulose, nitrodextran, nitroagarose, nitrodextrin, nitroamylose, nitroamylopectin, nitroglycogen, nitropullulan, nitromannan, nitroglucomannan, nitrolichenin, nitroisolichenin, nitrolaminarin, nitrocarrageenan, nitroxylan, nitrofructan, nitroalginic acid, nitrohyaluronic acid, nitrochondroitin, nitrochitin and nitrochitosan are preferably used.

Saponification products of nitrocellulose, nitrohemicellulose, nitrodextran, nitroagarose, nitrodextrin, nitroamylose, nitroamylopectin, nitroglycogen, nitropullulan, nitromannan, nitroglucomannan, nitrolichenin, nitroisolichenin, nitrolaminarin, nitrocarrageenan, nitroxylan, nitrofructan, nitroalginic acid, nitrohyaluronic acid, nitrochondroitin, nitrochitin and nitrochitosan, all of which have been mentioned above, are also more preferably used.

As the sulfate ester of one of the aforementioned polysaccharide structures, cellulose sulfate, hemicellulose sulfate, dextran sulfate, agarose sulfate, dextrin sulfate, amylose sulfate, amylopectin sulfate, glycogen sulfate, pullulan sulfate, mannan sulfate, glucomannan sulfate, lichenin sulfate, isolichenin sulfate, laminarin sulfate, carrageenan sulfate, xylan sulfate, fructan sulfate, alginic acid sulfate, hyaluronic acid sulfate, chondroitin sulfate, chitin sulfate and chitosan sulfate are preferably used. Further, saponification products of cellulose sulfate, hemicellulose sulfate, dextran sulfate, agarose sulfate, dextrin sulfate, amylose sulfate, amylopectin sulfate, glycogen sulfate, pullulan sulfate, mannan sulfate, glucomannan sulfate, lichenin sulfate, isolichenin sulfate, laminarin sulfate, carrageenan sulfate, xylan sulfate, fructan sulfate, alginic acid sulfate, hyaluronic acid sulfate, chondroitin sulfate, chitin sulfate and chitosan sulfate, all of which have been mentioned above, are also more preferably used.

As the sulfonate ester of one of the aforementioned polysaccharide structures, those selected from one of an alkyl sulfonate ester, an alkenyl sulfonate ester, an aromatic sulfonate ester and an aromatic alkyl sulfonate ester are preferred. Saponification products of one of the aforementioned polysaccharide structures having an alkyl sulfonate ester, an alkenyl sulfonate ester, an aromatic sulfonate ester and an aromatic alkyl sulfonate ester can also be more preferably used.

As the phosphate ester of one of the aforementioned polysaccharide structures, cellulose phosphate, hemicellulose phosphate, dextran phosphate, agarose phosphate, dextrin phosphate, amylose phosphate, amylopectin phosphate, glycogen phosphate, pullulan phosphate, mannan phosphate, glucomannan phosphate, lichenin phosphate, isolichenin phosphate, laminarin phosphate, carrageenan phosphate, xylan phosphate, fructan phosphate, alginic acid phosphate, hyaluronic acid phosphate, chondroitin phosphate, chitin phosphate and chitosan phosphate can be preferably used. Moreover, saponification products of cellulose phosphate, hemicellulose phosphate, dextran phosphate, agarose phosphate, dextrin phosphate, amylose phosphate, amylopectin phosphate, glycogen phosphate, pullulan phosphate, mannan phosphate, glucomannan phosphate, lichenin phosphate, isolichenin phosphate, laminarin phosphate, carrageenan phosphate, xylan phosphate, fructan phosphate, alginic acid phosphate, hyaluronic acid phosphate, chondroitin phosphate, chitin phosphate and chitosan phosphate, all having been mentioned above, can also be more preferably used.

As the phosphonate ester of one of the aforementioned polysaccharide structures, cellulose phosphonate, hemicellulose phosphonate, dextran phosphonate, agarose phosphonate, dextrin phosphonate, amylose phosphonate, amylopectin phosphonate, glycogen phosphonate, pullulan phosphonate, mannan phosphonate, glucomannan phosphonate, lichenin phosphonate, isolichenin phosphonate, laminarin phosphonate, carrageenan phosphonate, xylan phosphonate, fructan phosphonate, alginic acid phosphonate, hyaluronic acid phosphonate, chondroitin phosphonate, chitin phosphonate and chitosan phosphonate can be preferably used. Further, saponification products of cellulose phosphonate, hemicellulose phosphonate, dextran phosphonate, agarose phosphonate, dextrin phosphonate, amylose phosphonate, amylopectin phosphonate, glycogen phosphonate, pullulan phosphonate, mannan phosphonate, glucomannan phosphonate, lichenin phosphonate, isolichenin phosphonate, laminarin phosphonate, carrageenan phosphonate, xylan phosphonate, fructan phosphonate, alginic acid phosphonate, hyaluronic acid phosphonate, chondroitin phosphonate, chitin phosphonate and chitosan phosphonate, all having been mentioned above, can also be more preferably used.

As the phosphate ester of one of the polysaccharide structures, cellulose pyrophosphate, hemicellulose pyrophosphate, dextran pyrophosphate, agarose pyrophosphate, dextrin pyrophosphate, amylose pyrophosphate, amylopectin pyrophosphate, glycogen pyrophosphate, pullulan pyrophosphate, mannan pyrophosphate, glucomannan pyrophosphate, lichenin pyrophosphate, isolichenin pyrophosphate, laminarin pyrophosphate, carrageenan pyrophosphate, xylan pyrophosphate, fructan pyrophosphate, alginic acid pyrophosphate, hyaluronic acid pyrophosphate, chondroitin pyrophosphate, chitin pyrophosphate and chitosan pyrophosphate are preferably used. Saponification products of cellulose pyrophosphate, hemicellulose pyrophosphate, dextran pyrophosphate, agarose pyrophosphate, dextrin pyrophosphate, amylose pyrophosphate, amylopectin pyrophosphate, glycogen pyrophosphate, pullulan pyrophosphate, mannan pyrophosphate, glucomannan pyrophosphate, lichenin pyrophosphate, isolichenin pyrophosphate, laminarin pyrophosphate, carrageenan pyrophosphate, xylan pyrophosphate, fructan pyrophosphate, alginic acid pyrophosphate, hyaluronic acid pyrophosphate, chondroitin pyrophosphate, chitin pyrophosphate and chitosan pyrophosphate can also be more preferably used.

As the ether derivative of one of the aforementioned polysaccharide structures, methyl cellulose, ethyl cellulose, carboxymethyl cellulose, carboxyethyl cellulose, carboxyethyl carbamoylethyl cellulose, hydroxymethyl cellulose, hydroxyethyl cellulose, hydroxypropyl cellulose, hydroxypropylmethyl cellulose, hydroxyethylmethyl cellulose, cyanoethyl cellulose and carbamoylethyl cellulose can be preferably used, but the invention is not limited thereto. Hydroxymethyl cellulose and hydroxyethyl cellulose can be preferably used.

One of the aforementioned polysaccharide structures in which the hydroxyl groups have been halogenated to an arbitrary substitution degree may also be preferably used.

The aforementioned cellulose ester derivatives will be described below. Examples of cellulose as a raw material of the aforementioned cellulose ester derivative include natural cellulose, such as cotton linter, wood pulp (e.g., hardwood pulp and softwood pulp), hemp, and cellulose formed during culturing of acetic acid bacteria, and materials obtained by subjecting the natural cellulose to acid hydrolysis, mechanical pulverization, blasting treatment, and extruding treatment under high temperatures, so as to adjust the polymerization degree thereof. Cellulose ester derivatives obtained from any raw material cellulose can be used, and may be used after mixing in some cases. Detailed description of the raw material cellulose is found, for example, in, Purasuchikku Zairyo Koza (Lectures on Plastic Materials) authored by Marusawa and Uda, vol. 17, Sen-iso-kei Jusi (Cellulose Fiber-based Resins), published by Nikkan Kogyo Shimbun, Ltd. (1970).

According to the aforementioned literature, the molecular weight of cellulose varies over a wide range. For example, natural cellulose has a molecular weight of from 600,000 to 1,500,000 (roughly from 3,500 to 10,000 in terms of polymerization degree), refined linter has a molecular weight of from 80,000 to 500,000 (roughly from 500 to 3,000 in terms of polymerization degree) and wood pulp has a molecular weight of from 80,000 to 1,340,000 (roughly from 500 to 2,100 in terms of polymerization degree). The molecular weight largely influences the strength property of cellulose or a derivative thereof. When the molecular weight is decreased beyond a certain polymerization degree, the mechanical strength thereof suddenly deteriorates, but such a material can be used as a raw material of the nucleic acid-adsorbing porous membrane in the invention without any problem.

As one example of the nucleic acid-adsorbing porous membrane, a porous membrane of a cellulose derivative obtained by esterification of cellulose can be used, but the aforementioned particularly preferred species of cellulose may not be used as they are, but are used as purified linter or purified high-quality wood pulp after purifying linter or pulp. Linter contains short fibers among cotton fibers of cottonseeds and exhibits a high content of α-cellulose (for example from 88 to 92% by mass) and a high purity with less impurity. (In this specification, mass ratio is equal to weight ratio.) Purified linter can be obtained by subjecting crude linter to dust removal, alkali steaming, bleaching, acid treatment, dehydration and drying. The details of these processes are disclosed in, Purasuchikku Zairyo Koza (Lectures on Plastic Materials) vol. 17, Sen-iso-kei Jusi (Cellulose Fiber-based Resins), authored by Marusawa and Uda, published by Nikkan Kogyo Shimbun, Ltd. (1970) on pages 25 to 28, and the characteristics of the materials are described in Table 2.3 of the literature, by which purified linter, which is more preferable for the invention, can be obtained.

In addition, purified pulp is also described in pages 28 to 32 of the same literature, and the characteristics thereof are set forth in Table 2.4. Pulp purified by the described methods is also preferably used as a raw material of the cellulose ester derivative. It is also preferred to use cotton linter and wood pulp, which have been purified, as a mixture, whereby the mixing ratio is preferably from 5/95 to 95/5, and more preferably 10/90 to 90/10, while it is not particularly limited thereto. The solubility of the material is improved by mixing, whereby the surface property and the mechanical characteristics of the porous membrane of the cellulose ester derivative can be improved.

The α-cellulose content, which is an index of pulp purity, can be selected, for example, from a range of about from 80 to 100% by mass, and is generally about from 85 to 98% for wood pulp. Low purity pulp, for example, pulp having an α-cellulose content of about from 80 to 96% (particularly from 92 to 96%) may also be used in the invention. Among these kinds of pulp, wood pulp is generally used.

Further, in the nucleic acid-adsorbing porous membrane of the invention, the neutral constituent sugar component in pulp of cotton, which mainly comprises glucose, may contain mannose and xylose as described in JP-A-11-130301. The ratio thereof is not particularly limited, and the ratio of mannose/xylose (molar ratio) is generally from 0.35/1 to 3.0/1, preferably from 0.35/1 to 2.5/1, and more preferably from 0.35/1 to 2/1. In the cellulose triacetate thus produced in this case, the total content of mannose and xylose is generally from 0.01 to 5% by mole, and preferably from 0.1 to 4% by mole. Mannose and xylose herein are major constituent sugars of hemicellulose (such as xylan and glucomannan) contained in pulp. The constituent sugar components of the raw material pulp and the cellulose ester derivative thus obtained (e.g., cellulose triacetate) can be analyzed by the method disclosed in JP-A-11-130301.

As the porous membrane of cellulose, a porous membrane of regenerated cellulose can be preferably used. As the example of the regenerated cellulose, one obtained by converting a surface or the whole of a solid of acetylcellulose to cellulose through saponification, one produced from a copper ammonia solution of cellulose, one produced from a viscose solution of cellulose, and one produced from an alkali solution of cellulose can be mentioned, all of which are different from original cellulose in crystalline state and the like. Cellulose includes crystal forms I, II, III and IV. Any of crystal forms can be preferably used in the invention, and cellulose used in the invention may contain the crystal forms I, II, III and IV in any proportions. With respect to a regenerated cellulose porous membrane produced from an acetylcellulose porous membrane, those obtained by the raw materials and the methods set forth in JP-B-45-4633 and JP-A-56-100604 may be used, but the invention is not limited thereto. As a regenerated cellulose porous membrane produced from a copper ammonia solution of cellulose, those obtained by the raw materials and the methods disclosed in JP-A-58-89625, JP-A-58-89626, JP-A-58-89627, JP-A-58-89628, JP-A-59-45333, JP-A-59-45334, JP-A-59-199728, JP-A-61-274707, JP-A-62-1403, JP-A-63-161972 and JP-A-7-330945 can be used, but the invention is not limited thereto. A regenerated cellulose porous membrane can be obtained by modifying the composition of the reaction solution and the coagulation method of a viscose solution obtained by effecting an alkali and carbon disulfide to cellulose, and can be used for the invention. As a regenerated cellulose porous membrane produced from an alkali solution of cellulose, those obtained by the raw materials and the methods set forth in JP-A-62-240328, JP-A-62-240329 and JP-A-1-188539 can be used, but the invention is not limited thereto.

In the nucleic acid-adsorbing porous membrane of the invention, the aforementioned cellulose ester derivative preferably has a viscosity average degree of polymerization of from 200 to 3,000. Further, such a cellulose ester derivative preferably has a ratio of weight average molecular weight to number average molecular weight of from 0.8 to 2. Still further, the cellulose ester derivative preferably contains an acid having an acid dissociation constant of from 1.93 to 4.5 or a salt thereof.

The aforementioned cellulose ester derivative preferably has a content of residual acetic acid or a fatty acid having 3 to 22 carbon atoms of 0.5% by mass or less. Further, the cellulose ester derivative preferably contains at least one kind of an alkali metal and/or an alkaline earth metal in an amount of from 1 ppb to 10,000 ppm. Still further, the aforementioned cellulose acylate preferably contains at least one kind of aluminum, bismuth, silicon and a heavy metal (such as chromium, manganese, iron, cobalt, nickel, copper, zinc, arsenic, silver, cadmium, tin, antimony, gold, platinum, mercury and lead) in an amount of from 1 ppb to 1,000 ppm.

Particularly preferred examples of the porous film of a cellulose ester derivative include a porous membrane of an organic high polymer composed of a mixture of plural kinds of acetylcellulose different from each other in acetyl value. As the mixture of plural kinds of acetylcellulose different from each other in acetyl value, a mixture of triacetylcellulose and diacetylcellulose, a mixture of triacetylcellulose and monoacetylcellulose, a mixture of triacetylcellulose, diacetylcellulose and monoacetylcellulose, and a mixture of diacetylcellulose and monoacetylcellulose are preferably used. In particular, a mixture of triacetylcellulose and diacetylcellulose can be preferably used. The mixing ratio (mass ratio) of triacetylcellulose and diacetylcellulose is preferably from 99/1 to 1/99, and more preferably from 90/10 to 50/50.

As regards the cellulose ester derivative, cellulose ester derivatives set forth in JP-A-10-45803, JP-A-11-269304, JP-A-8-231761, JP-A-10-60170, JP-A-9-40792, JP-A-11-5851, JP-A-11-269304, JP-A-9-90101, JP-A-57-182737, JP-A-4-277530, JP-A-11-292989, JP-A-12-131524 and JP-A-12-137115 are also preferably used. The nucleic acid-adsorbing porous membrane of the invention is not particularly limited to these materials.

X-ray analysis is also used as a measure for evaluating the structure of cellulose. It is described that, according to the analysis, cellulose molecules are aligned in parallel to the direction of fiber axis and attract each other through hydrogen bond, and that one unit cell is formed of a cellulose unit containing five cellulose molecules. The X-ray analytical method shows that the degree of crystallinity is about 70% for natural cellulose, and these kinds of cellulose can be used for producing the cellulose ester derivative for the invention.

Analysis of cellulose for use in the invention is carried out by a variety of methods, details of which are described in ASTM Standard Part 15, TAPPI Standard (Technical Association of the Pulp and Paper Industry), JIS P 8101. The measuring item includes ash content, the contents of calcium oxide and magnesium oxide, α-cellulose, β-cellulose and copper value.

Saponification means an operation of bringing an ester derivative into contact with a saponification treatment solution (exemplified by a sodium hydroxide aqueous solution). By the operation, the ester moiety of the ester derivative having been in contact with the saponification treatment solution is hydrolyzed to introduce a hydroxyl group. In order to change the saponification degree, the saponification treatment is carried out by changing the concentration of sodium hydroxide, the treating temperature and the treating time. The saponification degree can be easily measured by NMR, IR or XPS (for example, through the decrement of the peak of a carbonyl group).

As the specific example of the porous membrane of an organic material having a polysaccharide structure, a surface-saponification product of acetylcellulose set forth in JP-A-2003-128691 is mentioned. The surface-saponification product of acetylcellulose is amaterial obtained by subjecting a mixture of plural kinds of acetylcellulose different in acetyl value to a saponification treatment, and a saponification product of a mixture of triacetylcellulose and diacetylcellulose, a saponification product of a mixture of triacetylcellulose and monoacetylcellulose, a saponification product of a mixture of triacetylcellulose, diacetylcellulose and monoacetylcellulose, and a saponification product of a mixture of diacetylcellulose and monoacetylcellulose can also be preferably used. More preferably, a saponification product of a mixture of triacetylcellulose and diacetylcellulose is to be used. The mixing ratio (mass ratio) of triacetylcellulose and diacetylcellulose is preferably from 99/1 to 1/99, and more preferably from 90/10 to 50/50. In this case, the amount (density) of hydroxyl groups at the solid phase surface can be controlled by the extent of the saponification treatment (saponification degree). In order to improve the separation efficiency of a nucleic acid, a larger amount (density) of hydroxyl group is preferred. For example, in the case of acetylcellulose, such as triacetylcellulose, the saponification degree (surface saponification degree) is preferably about 5% or more, and more preferably 10% or more. In order to increase the surface area of an organic high polymer having a hydroxyl group, it is preferred that a porous membrane of acetylcellulose is subjected to a saponification treatment, whereby use of a porous membrane having front and back surfaces symmetrical with each other is preferred due to the merit of production without discrimination between the front and back surfaces of the membrane. Independently, a porous membrane having front and back surfaces asymmetrical with each other can be preferably used due to the merit of reducing the risk of choking.

As a method for introducing a hydrophilic group to a porous membrane of an organic material having no hydrophilic group, a graft polymer chain having a hydrophilic group in the polymer chain or a side chain thereof can be bonded to the porous membrane. The method of bonding the graft polymer chain to the porous membrane of the organic material includes two methods, i.e., a method of chemically bonding the graft polymer chain to the porous membrane, and a method of polymerizing a compound having a polymerizable double bond from the porous membrane as a starting point to form the graft polymer chain.

Firstly, in the method of attaching the graft polymer chain to the porous membrane through chemical bond, a polymer having a functional group capable of reacting with the porous membrane at an end or a side chain of the polymer is used, and the functional group and a functional group on the porous membrane are chemically reacted to achieve grafting. The functional group capable of reacting the porous membrane is not particularly limited so far as it is capable of reacting with the functional group on the porous membrane, and examples thereof include a silane coupling group, such as alkoxysilane, an isocyanate group, an amino group, a hydroxyl group, a carboxyl group, a carbonyl group, a sulfonic acid group, a phosphoric acid group, an epoxy group, an allyl group, a methacryloyl group, an acryloyl group, an amide group, a hydrazide group, an aldehyde group, a thiol group and a succinimide group.

As the example of a compound that is particularly useful as the polymer having a reactive functional group at an end or a side chain of the polymer, a polymer having a trialkoxysilyl group at an end of the polymer, a polymer having an amino group at an end of the polymer, a polymer having a carboxyl group at an end of the polymer, a polymer having an epoxy group at an end of the polymer, and a polymer having an isocyanate group at an end of the polymer are mentioned. The polymer used herein is not particularly limited so far as it has such a hydrophilic group that participates in the adsorption of a nucleic acid, and specifically polyhydroxyethyl acrylate and polyhydroxyethyl methacrylate, and salts thereof, polyvinyl alcohol, polyvinylpyrrolidone, polyacrylic acid and polymethacrylic acid, and salts thereof, polyoxyethylene, polylactic acid, polyketone, polyetherimide, polyamideimide, polyphenylene sulfone, polyphenylene sulfide sulfone, nylon, N-methyl modified nylon, N-alkoxymethyl modified nylon, N-alkylthiomethyl modifiednylon, polysulfone, polyethersulfone, polyarylsulfone, polyallylsulfone, polyallylamine and polyurethane are mentioned.

The method of polymerizing a compound having a polymerizable double bond from the porous membrane as a starting point to form the graft polymer chain is generally referred to as a surface graft polymerization. The term 'surface graft polymerization method' designates such a method that a surface of a porous membrane as a substrate is provided with an active species by plasma irradiation, light irradiation or heating, to which a compound having a polymerizable double bond disposed to be in contact with the porous membrane is bonded through polymerization.

It is necessary that the compound useful for forming a graft polymer chain bonded to the substrate satisfies two requirements, i.e., it has a polymerizable double bond, and it has a hydrophilic group capable of participating in the adsorption of a nucleic acid. As such a compound, any of polymer, oligomer and monomer having a hydrophilic group can be used as far as they have a double bond in the molecules thereof Particularly useful compounds are monomers having a hydrophilic group.

As the specific example of the useful monomer having a hydrophilic group, the following monomers can be mentioned. For example, a monomer having a hydroxyl group, such as 2-hydroxyethyl acrylate, 2-hydroxyethyl methacrylate and glycerol monomethacrylate, can be preferably used in particular. Moreover, a carboxyl group-containing monomer, such as acrylic acid and methacrylic acid, and an alkali metal salt, an amine salt and an acrylamide thereof can also be preferably used.

As another method for introducing a hydrophilic group to a porous membrane of an organic material having no hydrophilic group, a method of coating a material having a hydrophilic group can be employed. The material used for coating is not particularly limited so far as it has a hydrophilic group capable of participating in the adsorption of a nucleic acid, and a polymer of an organic material is preferred from the standpoint of easiness in operation. Examples of the polymer include polyhydroxyethyl acrylate and polyhydroxyethyl methacrylate, and salts thereof, polyvinyl alcohol, polyvinylpyrrolidone, polyacrylic acid and polymethacrylic acid, and salts thereof, polyoxyethylene, acetylcellulose and a mixture of plural kinds of acetylcellulose different in acetyl value, and a polymer having a polysaccharide structure is preferred.

It is also possible that acetylcellulose or a mixture of plural kinds of acetylcellulose different in acetyl value is coated on a porous membrane of an organic material having no hydrophilic group, and then the acetylcellulose or the mixture of plural kinds of acetylcellulose different in acetyl value thus coated is subjected to a saponification treatment. In this case, the saponification degree is preferably about 5% or more, and more preferably about 10% or more.

As a porous membrane of an inorganic material having a hydrophilic group, a porous membrane containing a silica compound can be mentioned. As the porous membrane containing a silica compound, one can mention a glass filter. In addition, the porous silica thin film set forth in Japanese Patent No. 3058342 can be mentioned. The porous silica thin film herein can be produced, by, after expanding an expansion solution of a cationic amphoteric substance capable of forming a bimolecular membrane on a substrate, removing the solvent from the liquid membrane on the substrate to prepare a multilayer bimolecular thin film of the amphoteric substance, then bringing the multilayer bimolecular thin film into contact with a solution containing a silica compound, and further removing by extraction the multilayer bimolecular thin film to obtain the porous silica thin film.

As the method for introducing a hydrophilic group to a porous membrane of an inorganic material having no hydrophilic group, there are the following two methods, i.e., a method of chemically bonding a graft polymer chain to the porous membrane, and a method of polymerizing a monomer having a polymerizable double bond and a hydrophilic group from the porous membrane as a starting point to form a graft polymer chain.

In the case of attaching the graft polymer chain to the porous membrane through chemical bond, a functional group capable of reacting with a functional group at an end of the graft polymer chain is introduced to the inorganic material, and the graft polymer is chemically bonded thereto. In the case of polymerizing a monomer having a polymerizable double bond and a hydrophilic group from the porous membrane as a starting point to form a graft polymer chain, a functional group capable of acting as the starting point of polymerization of the compound having a double bond is introduced to the inorganic compound.

As the graft polymer having a hydrophilic group and the monomer having a polymerizable double bond and a hydrophilic group in the molecule, the graft polymers having a hydrophilic group and the monomers having a hydrophilic group and a double bond in the molecule set forth in the method of chemically bonding the graft polymer chain to the porous membrane of an organic material having no hydrophilic group are preferably used.

As another method for introducing a hydrophilic group to a porous membrane of an inorganic material having no hydrophilic group, a material having a hydrophilic group may be used for coating. The material used for coating is not particularly limited so far as it has a hydrophilic group capable of participating in the adsorption of a nucleic acid, and a polymer of an organic material is preferred from the viewpoint of operational facility. As such a polymer, polyhydroxyethyl acrylate and polyhydroxyethyl methacrylate, and salts thereof, polyvinyl alcohol, polyvinylpyrrolidone, polyacrylic acid and polymethacrylic acid, and salts thereof, polyoxyethylene, acetylcellulose and a mixture of plural kinds of acetylcellulose different in acetyl value can be mentioned.

As the porous membrane of an inorganic material having no hydrophilic group, those obtained by processing a metal such as aluminum, glass, cement, ceramics such as pottery and porcelain, new ceramics, silicon, activated carbon, and aluminosilicate can be mentioned.

It is also possible that acetylcellulose or a mixture of plural kinds of acetylcellulose different in acetyl value is coated on a porous membrane of an inorganic material having no hydrophilic group, and then the acetylcellulose or the mixture of plural kinds of acetylcellulose different in acetyl value thus coated is subjected to a saponification treatment. In this case, the saponification degree is preferably about 5% or more, and more preferably about 10% or more.

In the aforementioned preparation process of the nucleic acid-adsorbing solid carrier, various kinds of additives corresponding to the use purposes (such as a plasticizer, an antistatic agent, a deterioration preventing agent, an ultraviolet ray inhibitor, a surfactant, a releasing agent, a coloring agent, a reinforcing agent and a crosslinking agent) may be added. The timing of addition may be any occasion during the dope preparing process, and the step of adding the additive may be carried out as the final step of the dope preparing process.

The nucleic acid-adsorbing solid carrier may contain a plasticizer depending on necessity. The phosphate esters and carboxylate esters disclosed in JP-A-2002-265636, the polyhydric alcohols disclosed in JP-A-2-6826, the (di)pentaerythritol esters disclosed in JP-A-5-194788, JP-A-60-250053, JP-A-4-227941, JP-A-6-16869, JP-A-5-271471, JP-A-7-286068, JP-A-5-5047, JP-A-11-80381, JP-A-7-20317, JP-A-8-57879, JP-A-10-152568, JP-A-10-120824 and JP-A-11-124445, the glycerol esters disclosed in JP-A-11-246704, the diglycerol esters disclosed in JP-A-2000-63560, the citrate esters disclosed in JP-A-11-92574, the substituted phenyl phosphate esters disclosed in JP-A-11-90946, and those disclosed in JP-A-56-100604 can be preferably used. The literatures cited herein contain various and a number of useful descriptions on the usage and characteristics of plasticizers in addition to those on plasticizers themselves, and such information can also be preferably utilized for the design of the nucleic acid-adsorbing solid carrier of the invention.

The aforementioned nucleic acid-adsorbing solid carrier of the invention may contain an antistatic agent for the purpose of preventing the membrane from being charged upon handling. As regards such an antistatic agent, an ionic electroconductive substance and electroconductive fine particles are preferably used. The ionic electroconductive substance herein designates such a substance that exhibits electroconductivity and contains ions as a carrier for carrying electricity, and as the example thereof, one can mention an ionic high polymer compound. As the ionic high polymer compound, the anionic high polymer compounds disclosed in JP-B-49-23828, JP-B-49-23827 and JP-B-47-28937, the ionene polymers having a dissociation group in the main chain disclosed in JP-B-55-734, JP-A-50-54672, JP-B-59-14735, JP-B-57-18175, JP-B-57-18176 and JP-B-57-56059, and the cationic pendant polymers having a cationic dissociation group on a side chain disclosed in JP-B-53-13223, JP-B-57-15376, JP-B-53-45231, JP-B-55-145783, JP-B-55-65950, JP-B-55-67746, JP-B-57-11342, JP-B-57-19735, JP-B-58-56858, JP-A-61-27853 and JP-B-62-9346 can be mentioned. Among these, what is preferred includes an electroconductive material in a fine particle form finely dispersed and incorporated in the nucleic acid-adsorbing solid carrier. As the preferable electroconductive material used for such a material, it is desirable to contain electroconductive fine particles of a metallic oxide or a complex oxide comprising the metallic oxide, and an ionene electroconductive polymer as disclosed in JP-A-9-203810 or a quaternary ammonium cationic electroconductive polymer particles having intermolecular crosslinks. The particle diameter is preferably from 5 nm to 10 µm, and a more preferred range of the diameter depends on the species of the fine particles used. Preferred examples of the metallic oxide as the electroconductive fine particles include ZnO, $TiO_2$, $SnO_2$, $Al_2O_3$, $In_2O_3$, $SiO_2$, MgO, BaO, $MoO_2$, $V_2O_5$ and complex oxides thereof. In particular, ZnO, $TiO_2$ and $SnO_2$ are preferred. As the example of the material containing a hetero atom, incorporation of Al or In to ZnO, incorporation of Nb and Ta to $TiO_2$, and incorporation of Sb, Nb and a halogen element to $SnO_2$ are effective. The addition amount of such a hetero atom is preferably from 0.01 to 25% by mole, and preferably from 0.1 to 15% by mole in particular. As the metallic oxide particles having electroconductivity, particles having a volume resistivity of $10^7$ Ω·cm or less, and particularly preferably $10^5$ Ω·cm or less, and a primary particle diameter of from 100 Å to 0.2 µm and a specified structure with a longitudinal diameter of the higher-order structure of from 30 nm to 6 µm are preferably contained in the nucleic acid-adsorbing solid carrier in an amount of from 0.01 to 20% in terms of volume fraction. In addition, since the crosslinked cationic electroconductive polymer as a dispersive particulate polymer has such characteristics that the cationic component inside the particles can be retained at a high concentration and a high density, it has not only excellent electroconductivity but also exhibits no deterioration in electroconductivity even under a low relative humidity condition. Further, though the particles thereof are well dispersed in the dispersed state, upon membrane formation, the particles exhibit good interparticulate adhesiveness at the membrane formation step after flow casting, and the membrane shows a high membrane strength and excellent chemical resistance. The dispersive particulate polymer as a crosslinking-type cationic electroconductive polymer generally is in a particle size range of about from 10 to 1,000 nm, and preferably from 20 to 300 nm. The dispersive particulate polymer herein is such a polymer that gives a solution with transparent or slightly turbid appearance under visual observation but observed as particle dispersion with an electron microscope. Moreover, an organic electronic electroconductive organic compound may also be used. Examples thereof include polythiophene, polypyrrole, polyaniline, polyacetylene and polyphosphazene. These materials are preferably used as a complex with polystyrene sulfonic acid or perchloric acid as an acid donating material.

To the aforementioned nucleic acid-adsorbing solid carrier, a deterioration preventing agent (such as an antioxidant, a peroxide decomposing agent, a radical inhibitor, a metal inactivating agent, an acid scavenger and an amine) and an ultraviolet ray inhibitor can be added. With respect to these deterioration preventing agents and the ultraviolet ray inhibitor, those disclosed in JP-A-60-235852, JP-A-3-199201, JP-A-5-190707, JP-A-5-194789, JP-A-5-271471, JP-A-6-107854, JP-A-6-118233, JP-A-6-148430, JP-A-7-11056, JP-A-7-11055, JP-A-8-29619, JP-A-8-239509, JP-A-2000-204173, JP-A-5-197073, JP-A-5-194789, JP-A-6-107854, JP-A-60-235852, JP-A-12-193821, JP-A-6-118233, JP-A-6-148430, JP-A-2002-265636 and JP-A-5-197073 can be preferably used. As particularly preferred examples of the deterioration preventing agent, dibutylhydroxytoluene (BHT) can be mentioned.

The addition amount of the deterioration preventing agent is preferably from 0.01 to 1% by mass, and more preferably from 0.01 to 0.08% by mass, based on the solution (dope) to be prepared. In the case where the addition amount is less than 0.01% by mass, substantially no effect of the deterioration preventing agent can be observed. In the case where the addition amount exceeds 1% by mass, there are some cases where the deterioration preventing agent is bled out to the surface of the solid carrier. The deterioration preventing agent used in the invention is preferably a liquid at 25° C. having a boiling point of 200° C. or higher or a solid having a melting point of from 25 to 250° C., and more preferably a liquid at 25° C. having a boiling point of 250° C. or higher or a solid having a melting point of from 25 to 200° C. In the case where the deterioration preventing agent is a liquid, it can be generally purified by distillation under reduced pressure. Thus, a higher degree of vacuum is preferred, such as, for example, 100 Pa or less. Further, it is particularly preferred to purify the agent by using a molecular distillation apparatus. In the case where the plasticizer is a solid, it is generally purified by recrystallization using a solvent, filtration, rinsing and drying.

To the aforementioned nucleic acid-adsorbing solid carrier, a surfactant may be added. With respect to the surfactant, those set forth in JP-A-2002-265636, JP-B-55-31418, Kaimen Kasseizai Tou Ichiranhyo (List of Surfactants, etc.), 2001 ed., published by Japan Surfactant Industry Association, and, Kaimen Kasseizai no Oyo (Applications of Surfactants), authored by Takao Kariyone and published by Saiwai Shobo Co., Ltd. on Sep. 1, 1980 can be preferably used, but the invention is not limited thereto. In the invention, preferred surfactants are not particularly limited in species and using amount thereof, and they can be used in such an amount that provides target surface-active characteristics.

To the aforementioned nucleic acid-adsorbing solid carrier, a releasing agent may also be added depending on necessity for reducing a load on releasing during the production thereof. A surfactant is effective as the releasing agent, which is not particularly limited and may be a phosphoric acid-based, a sulfonic acid-based, a carboxylic acid-based, anonionic and a cationic ones. These are set forth, for example, in JP-A-61-243837 and JP-A-2000-99847. Moreover, an acid having an acid dissociation constant pKa of from 1.93 to 4.50 (preferably from 2.0 to 4.4, more preferably from 2.2 to 4.3 (for example from 2.5 to 4.0), and particularly preferably from 2.6 to 4.3 (for example from 2.6 to 4.0) or a salt thereof set forth in JP-A-10-316701 is preferred as the releasing agent. These acids may be either inorganic or organic. With respect to pKa of an acid, Kagaku Binran (Chemical Handbook), 3rd revised edition, Basic Edition II, edited by the Chemical Society of Japan, published by Maruzen Co., Ltd. maybe referred to. In addition, the releasing agents set forth in JP-A-2002-265636 may also be preferably used. The literatures cited herein contain various and a number of useful descriptions on the usage and characteristics of releasing agents in addition to those on releasing agents themselves, and such information can also be preferably utilized for the design of the nucleic acid-adsorbing solid carrier of the invention.

To the aforementioned nucleic acid-adsorbing solid carrier, a coloring agent may be added. With respect to the coloring agent, organic, inorganic and organic/inorganic complex coloring agents having been known in the art, such as a dye, a pigment, an oxidation coloring dye, a reduction coloring dye, a pH indicator, a fluorescent dye, a coupling dye, an ultraviolet ray-absorbing dye, an infrared ray-absorbing dye, a near infrared ray-absorbing dye, a pressure-sensitive dye, a photochromic dye, a thermochromic dye, an electrochromic dye, an organic luminescent dye, a photoelectric conversion dye, a spectral sensitizing dye, a dichromatic dye, an electroluminescent dye, a dye for foodstuff, an organic non-linear optical dye, a chemical luminescent dye, a dye for medical products, a dye for medical diagnosis, a dye for cosmetics, a semiconductor laser dye, a sublimation transfer dye, a melt transfer dye, a thermosensitive dye, a leuco dye, an electromagnetic wave-absorbing dye, a photoconductive dye and an electrostatic dye, can be used solely or in combination of plural kinds thereof in a desired concentration. Further, they may also be used together with a dispersant such as a surfactant and a protective polymer in a desired concentration, but the invention is not limited thereto.

To the aforementioned nucleic acid-adsorbing solid carrier, a reinforcing agent may be incorporated for the purpose of membrane strength enhancement. As the reinforcing agent, glass fibers, carbon fibers, silicon fibers, cellulose fibers, pulp fibers, potassium titanate fibers, silicon carbide whiskers, silicon nitride whiskers, zinc oxide whiskers, aluminum borate whiskers, basic magnesium sulfate and fibrous zonolite, potassium titanate whiskers, silicon carbide (SiC) whiskers, and calcium carbonate in a whisker form can be preferably used. But the invention is not limited thereto, and any material in a fibrous form or an acicular crystal form may be used. Moreover, a synthetic polymer may be added for improving the flexural strength whereby the polyurethane disclosed in JP-A-54-11081 can be preferably used, but the invention is not limited thereto.

To the aforementioned nucleic acid-adsorbing solid carrier, a crosslinking agent may be added. As regards the crosslinking agent, known materials may be used, and it is preferred to select an appropriate species depending on the functional group of the material of the solid carrier. In the case where the functional group is a hydroxyl group, crosslinking agents disclosed in JP-A-7-256066 and JP-A-3-68431 can be preferably used, but the invention is not limited thereto.

To the aforementioned nucleic acid-adsorbing solid carrier, a moistening agent may be added. As regards the moistening agent, those set forth in JP-A-63-262550, JP-A-63-262549 and JP-B-55-31418 can be preferably used, but the invention is not limited thereto.

The aforementioned nucleic acid-adsorbing porous membrane is capable of transmitting a solution therethrough and generally has a thickness of from 10 to 500 µm, and more preferably from 50 to 250 µm. The thickness is preferably as thin as possible from the viewpoint of ease in rinsing.

The aforementioned nucleic acid-adsorbing porous membrane capable of transmitting a solution therethrough has a minimum pore diameter of 0.22 µm or more, and more preferably 0.5 µm or more. In addition, as the nucleic acid-adsorbing porous membrane capable of transmitting a solution therethrough, one that has a ratio of the maximum pore diameter to the minimum pore diameter of 2 or more is preferably used. According to such constitution, not only a surface area sufficient for adsorbing a nucleic acid can be obtained, but also the membrane can be prevented from choking. A membrane with the ratio of the maximum pore diameter to the minimum pore diameter is 5 or more is more preferably used.

The aforementioned nucleic acid-adsorbing porous membrane capable of transmitting a solution therethrough has a porosity of from 50 to 95%, and preferably from 65 to 80%. The nucleic acid-adsorbing porous membrane capable of transmitting a solution therethrough has a bubble point of from 0.1 to 10 kgf/cm$^2$, and preferably from 0.2 to 4 kgf/cm$^2$.

As the aforementioned nucleic acid-adsorbing porous membrane capable of transmitting a solution therethrough, such a porous membrane is preferably used that has a pressure loss of from 0.1 to 100 kPa. With such a pressure loss, a uniform pressure can be obtained upon application of pressure. More preferably, such a porous membrane can be used that has a pressure loss of from 0.5 to 50 kPa. The pressure loss referred herein is a minimum pressure necessary for transmitting water per 100 µm in terms of membrane thickness.

As the aforementioned nucleic acid-adsorbing porous membrane capable of transmitting a solution therethrough, such a porous membrane can be used that has a water penetration amount upon transmitting water at a pressure of 1 kg/cm$^2$ at 25° C. of from 1 to 5,000 mL per 1 minute and 1 cm$^2$ of the membrane, and more preferably such a porous membrane can be used that has a water penetration amount upon transmitting water at a pressure of 1 kg/cm$^2$ at 25° C. of from 5 to 1,000 mL per 1 minute and 1 cm$^2$ of the membrane.

As the aforementioned nucleic acid-adsorbing porous membrane capable of transmitting a solution therethrough, such a porous membrane is preferably used that has an adsorption amount of a nucleic acid of 0.1 µg or more per 1 mg of the porous membrane, and such a porous membrane is more preferably used that has an adsorption amount of a nucleic acid of 0.9 µg or more per 1 mg of the porous membrane.

As the aforementioned nucleic acid-adsorbing porous membrane capable of transmitting a solution therethrough, such a porous membrane is preferably used that is formed of a cellulose derivative and is not dissolved within 1 hour, but is dissolved within 48 hours upon immersing the porous membrane of 5 mm square in 5 mL of trifluoroacetic acid. Such a membrane is also preferably used that is formed of a cellulose derivative and is dissolved within 1 hour upon immersing the porous membrane of 5 mm square in 5 mL of trifluoroacetic acid, but is not dissolved within 24 hours upon immersing in 5 mL of dichloromethane.

In the case of transmitting a sample solution containing a nucleic acid through the nucleic acid-adsorbing porous membrane, it is preferred that the sample solution is transmitted from one surface of the membrane to the other surface thereof from the standpoint that the sample solution can be brought into uniform contact with the porous membrane. In the case of transmitting a sample solution containing a nucleic acid through the nucleic acid-adsorbing porous membrane, it is preferred that the sample solution is transmitted from the side having a larger pore diameter to the side having a smaller pore diameter from the standpoint that the membrane is prevented from choking.

Upon transmitting a sample solution containing a nucleic acid through the nucleic acid-adsorbing porous membrane, the flow rate of the solution is preferably from 2 to 1,500 µL/sec per 1 cm$^2$ of the membrane in order to obtain a suitable contact time of the solution with the porous membrane. In the case where the contact time of the solution with the porous membrane is too small, sufficient separation and purification effects may not be attained, and too long a contact time is not preferred from the standpoint of operational facility. The flow rate is more preferably from 5 to 700 µL/sec per 1 cm$^2$ of the membrane.

With respect to the nucleic acid-adsorbing porous membrane capable of transmitting a solution in use therethrough, the number thereof may be one or plural. The plural nucleic acid-adsorbing porous membranes may be the same as or different from each other.

A nucleic acid separation and purification cartridge accommodating the nucleic acid-adsorbing porous membrane capable of transmitting a solution therethrough as described above in a vessel having at least two openings can be preferably used. Moreover, a nucleic acid separation and purification cartridge accommodating a plurality of the nucleic acid-adsorbing porous membranes capable of transmitting a solution therethrough as described above in a vessel having at least two openings can be preferably used. In the latter case, the plural nucleic acid-adsorbing porous membranes housed in the vessel having at least two openings may be the same as or different from each other.

The plural nucleic acid-adsorbing porous membranes may be a combination of the nucleic acid-adsorbing porous membrane of an inorganic material and the nucleic acid-adsorbing porous membrane of an organic material. For example, a combination of a glass filter and a porous membrane of regenerated cellulose may be mentioned. Further, the plural nucleic acid-adsorbing porous membranes may be a combination of the nucleic acid-adsorbing porous membrane of an inorganic material and a nucleic acid-non-adsorbing porous membrane of an organic material. For example, a combination of a glass filter and a porous membrane of nylon or polysulfone may be mentioned.

The nucleic acid-adsorbing porous membrane having been described hereinabove may have other forms than a membrane depending on the shape of the cartridge. For example, it may have a chip form or a block form.

It is preferred that the nucleic acid separation and purification cartridge accommodates, in the vessel having at least two openings, nothing but the nucleic acid-adsorbing porous membrane capable of transmitting a solution therethrough. As the material of the aforementioned vessel, plastics such as polypropylene, polystyrene, polycarbonate and polyvinyl chloride can be used. Further, a biodegradable material can also be preferably used. The vessel may be transparent or colored.

As the nucleic acid separation and purification cartridge, one equipped with a means for discriminating the individual cartridges for separation and purification of a nucleic acid can be used. As the means for discriminating the individual cartridges for separation and purification of a nucleic acid, a bar code and a magnetic tape can be mentioned.

Further, the nucleic acid separation and purification cartridge, which has such a mechanism that facilitates takeoff of the nucleic acid-adsorbing porous membrane from the vessel having at least two openings, may also be used.

A nucleic acid can be separated and purified by using the nucleic acid separation and purification cartridge having accommodated therein the nucleic acid-adsorbing porous membrane capable of transmitting each solution therethrough, via the following steps, i.e., (a) a step of injecting a sample solution containing a nucleic acid into one opening of the nucleic acid separation and purification cartridge accommodating the nucleic acid-adsorbing porous membrane capable of transmitting a solution therethrough in the vessel having at least two openings, (b) a step of pressurizing the interior of the nucleic acid separation and purification cartridge by using a pressure difference generating apparatus connected to the one opening of the nucleic acid separation and purification cartridge, so as to pass the injected sample solution containing a nucleic acid through the nucleic acid-adsorbing porous membrane and to discharge the solution from the other opening of the nucleic acid separation and purification cartridge, whereby the nucleic acid is adsorbed in the nucleic acid-adsorbing porous membrane, (c) a step of injecting a rinsing solution to the one opening of the nucleic acid separation and purification cartridge, (d) a step of pressurizing the interior of the nucleic acid separation and purification cartridge by using a pressure difference generating apparatus connected to the one opening of the nucleic acid separation and purification cartridge, so as to pass the injected rinsing solution through the nucleic acid-adsorbing porous membrane and to discharge the solution from the other opening of the nucleic acid separation and purification cartridge, whereby the nucleic acid-adsorbing porous membrane having the nucleic acid adsorbed therein is rinsed, (e) a step of injecting a recovering solution to the one opening of the nucleic acid separation and purification cartridge, and (f) a step of pressurizing the interior of the nucleic acid separation and purification cartridge by using a pressure difference generating apparatus connected to the one opening of the nucleic acid separation and purification cartridge, so as to pass the injected recovering solution through the nucleic acid-adsorbing porous membrane and to discharge the solution from the other opening of the nucleic acid separation and purification cartridge, whereby the nucleic acid is desorbed from the nucleic acid-adsorbing porous membrane and discharged to the outside of the nucleic acid separation and purification cartridge.

In each of the aforementioned steps (b), (d) and (f), the sample solution containing a nucleic acid, the rinsing solution or the recovering solution is passed through the nucleic acid-adsorbing porous membrane under the pressurized condition, and more preferably, in each of the aforementioned steps (b), (d) and (f), the sample solution containing a nucleic acid, the rinsing solution or the recovering solution is injected to the one opening of the nucleic acid separation and purification cartridge accommodating the nucleic acid-adsorbing porous membrane capable of transmitting a solution therethrough in the vessel having at least two openings, the interior of the cartridge is pressurized by using a pressure difference generating apparatus connected to the one opening of the cartridge, so as to pass the solution thus injected and to discharge the solution from the other opening. By passing the sample solution containing a nucleic acid, the rinsing solution or the recovering solution through the porous membrane under the pressurized condition, the apparatus can be favorably miniaturized and automated. The pressurizing operation is preferably carried out at a pressure of about from 10 to 200 kPa, and more preferably about from 40 to 100 kPa.

In the aforementioned process for separation and purification of a nucleic acid, the steps of from the first injection of a sample solution containing a nucleic acid to the last step of obtaining the nucleic acid outside the nucleic acid separation and purification cartridge can be completed within 10 minutes, and under favorable conditions within 2 minutes. In the process for separation and purification of a nucleic acid, the nucleic acid can be recovered at a yield of 50% by mass or more based on the total amount of the nucleic acid contained in the sample, and under favorable conditions 90% by mass or more.

In the process for separation and purification of a nucleic acid, such a nucleic acid can be recovered that has a wide range of molecular weight, such as from 1 to 200 kbp, and particularly from 20 to 140 kbp. In other words, a nucleic acid having a longer chain can be recovered in comparison to the spin column method using a glass filter having been conventionally practiced.

In the process for separation and purification of a nucleic acid, such a nucleic acid can be recovered that has a purity of from 1.6 to 2.0 for DNA and from 1.8 to 2.2 for RNA in terms of the value measured with an ultraviolet and visible spectrophotometer (260 nm/280 nm), and thus a nucleic acid having high purity with a small amount of impurities can be steadily obtained. Furthermore, such a nucleic acid can be recovered that has a purity of around 1.8 for DNA and around 2.0 for RNA in terms of the value measured with an ultraviolet and visible spectrophotometer (260 nm/280 nm).

The sample measured in the invention is not particularly limited, and in the diagnostic field, solutions prepared from biomaterials are measured, such as a biological fluid collected as an analyte, e.g., whole blood, blood plasma, blood serum, urine, faeces, semen and saliva, a plant (or a part thereof), an animal (or a part thereof), a bacterium, a virus, and a dissolved product or a homogenate thereof.

The analyte is then treated with an aqueous solution containing a reagent capable of dissolving a cell membrane and a nuclear membrane to solubilize a nucleic acid (a nucleic acid solubilizing reagent). By such treatment, a cell membrane and a nuclear membrane are dissolved to disperse a nucleic acid in the aqueous solution, whereby a sample solution containing a nucleic acid is obtained.

In order to solubilize a nucleic acid by dissolving a cell membrane and a nuclear membrane to, in the case where a sample to be analyzed is whole blood, for example, the following steps are required, i.e., (1) removal of erythrocytes, (2) removal of various proteins, and (3) dissolution of leukocytes and dissolution of a nuclear membrane. The step (1) of removal of erythrocytes and the step (2) of removal of various proteins are required for preventing the porous membrane from suffering nonspecific adsorption and choking, and the step (3) of dissolution of leukocytes and dissolution of a nuclear membrane is required for solubilizing a nucleic acid, which is the target of extraction. In particular, the step (3) of dissolution of leukocytes and dissolution of a nuclear membrane is an important step, and in the process of the invention, it is necessary to solubilize a nucleic acid by this step.

The analyte containing a nucleic acid may be an analyte containing a sole nucleic acid or an analyte containing plural different kinds of nucleic acid. The species of a nucleic acid to be recovered is not particularly limited and includes DNA and RNA. The number of the analyte may be one or a plurality (plural analytes may be processed in parallel to each other by using plural vessels). The length of a nucleic acid to be recovered is also not particularly limited, and for example, a nucleic acid having an arbitrary length of from several bp to several Mbp can be used. The length of a nucleic acid to be recovered is generally from several bp to several hundreds kbp from the operational viewpoint. In the method of separation and purification of a nucleic acid according to the invention, a nucleic acid having a relatively larger length can be rapidly recovered in comparison to the conventional simplified method of separation and purification of a nucleic acid, and the present method can be employed to recover a nucleic acid having a length of 50 kbp or more, more preferably 70 kbp or more, and further preferably 100 kbp or more. It is preferred to mildly carry out operations of stirring and pipetting for recovering DNA having a larger length.

In the following, the step of dissolving a cell membrane and a nuclear membrane, solubilizing a nucleic acid, and obtaining a sample solution containing a nucleic acid from an analyte will be described. In the invention, a nucleic acid solubilizing reagent is used for dissolving a cell membrane and a nuclear membrane to solubilize a nucleic acid. Examples of the nucleic acid solubilizing reagent include a solution containing a compound selected from a chaotropic salt, a surfactant, a defoaming agent, a protease, and a nucleic acid stabilizing agent.

As the step of dissolving a cell membrane and a nuclear membrane and solubilizing a nucleic acid to obtain a sample solution containing a nucleic acid from an analyte, a method including; (I) a step of injecting an analyte containing a cell or a virus into a vessel, (II) a step of adding a nucleic acid solubilizing reagent to the vessel to mix the analyte and the nucleic acid solubilizing reagent, (III) a step of incubating the mixed solution obtained in the preceding step, and (IV) a step of adding a water-soluble organic solvent to the mixed solution thus incubated, can be mentioned.

In the step of dissolving a cell membrane and a nuclear membrane and solubilizing a nucleic acid to obtain a sample solution containing a nucleic acid from an analyte, the analyte is subjected to homogenizing treatment to improve the adaptability to automated processing. Examples of the homogenizing treatment include an ultrasonic treatment, one using sharply edged projections, one based on high-speed agitation, one based on extrusion from minute gaps, and one using glass beads.

In the step of dissolving a cell membrane and a nuclear membrane and solubilizing a nucleic acid to obtain a sample solution containing a nucleic acid from an analyte, a nucleic acid solubilizing reagent containing a protease may be used, whereby the recovering amount and the recovering efficiency of a nucleic acid are improved to facilitate reduction of the necessary amount of the analyte containing a nucleic acid in concern and acceleration of the process speed.

As the protease, at least one selected from serine protease, cysteine protease and metal protease may be preferably used. Moreover, as the protease, a mixture of plural kinds of proteases may also be preferably used. The serine protease is not particularly limited, and for example, protease K may be preferably used. The cysteine protease is not particularly limited, and for example, papain and cathepsin can be preferably used. The metal protease is not particularly limited, and for example, carboxy peptidase can be preferably used. The protease is preferably used in a concentration of from 0.001 to 10 IU, and more preferably from 0.01 to 1 IU, per 1 mL of the total amount of the reaction system upon addition of the protease.

As the protease, a protease containing no nuclease can be preferably used. Further, a protease containing a stabilizer is preferably used. As the stabilizer a metallic ion can be preferably used. Specifically, magnesium ion is preferred, which may be added, for example, in the form of magnesium chloride. The addition of the stabilizer to the protease enables reduction of the amount of the protease necessary for recovering a nucleic acid, leading to reduction of the cost necessary for recovering a nucleic acid. The stabilizer for a protease is preferably contained in a concentration of from 1 to 1,000 mmol/l, and more preferably from 10 to 100 mmol/l, based on the total amount of the reaction system.

The protease may be used for recovering a nucleic acid as a single reagent obtained by mixing beforehand with other reagents such as a chaotropic salt and a surfactant. Moreover, the protease may be supplied as two or more reagents separately from the other reagent such as a chaotropic salt and a surfactant. In the later case, a reagent containing the protease is firstly mixed with an analyte, and then a reagent containing a chaotropic salt and a surfactant is mixed therewith. It is also possible to mix the protease after mixing a reagent containing a chaotropic salt or a surfactant in advance. Alternatively, the protease may be added dropwise just like eye drops from a protease storage container to a mixed solution of an analyte and a reagent containing a chaotropic salt and a surfactant. In this case, the operation can be simplified.

The concentration of a chaotropic salt in the nucleic acid solubilizing reagent is preferably 0.5 mol/l or more, more preferably from 0.5 to 4 mol/l, and further preferably from 1 to 3 mol/l. As the aforementioned chaotropic salt, guanidine hydrochloride is preferred, and other chaotropic salts (guanidine isothiocyanate, guanidine thiocyanate, urea, a guanidine salt, sodium isothiocyanate, sodium iodide and potassium iodide) can also be used. These salts may be used individually or in combination of a plurality thereof.

As the surfactant, a nonionic surfactant, a cationic surfactant, an anionic surfactant and an amphoteric surfactant can be mentioned. In the invention, a nonionic surfactant is preferably used. As the nonionic surfactant, a polyoxyethylene alkyl phenyl ether surfactant, a polyoxyethylene alkyl ether surfactant, and a fatty acid alkanol amide surfactant can be used, and a polyoxyethyelne alkyl ether surfactant is preferably used. More preferred are polyoxyethylene alkyl ether surfactants selected from POE decyl ether, POE lauryl ether, POE tridecyl ether, POE alkylene decyl ether, POE sorbitan monolaurate, POE sorbitan monooleate, POE sorbitan monostearate, polyoxyethylene sorbit tetraoleate, POE alkylamine and POE acetylene glycol.

Further, a cationic surfactant can also be preferably used. More preferred cationic surfactants include those selected from cetyltrimethylammonium bromide, dodecyltrimethylammonium chloride, tetradecyltrimethylammonium chloride and cetylpyridinium chloride.

These surfactants may be used individually or in combination of plural kinds thereof. The concentration of such a surfactant in the nucleic acid solubilizing reagent solution is preferably from 0.1 to 20% by mass.

In the case of recovering a nucleic acid other than RNA, e.g., DNA, a ribonuclease is preferably added to a nucleic acid solubilizing reagent solution in the step of dissolving a cell membrane and a nuclear membrane and solubilizing a nucleic acid to obtain a sample solution containing a nucleic acid from an analyte. In this case, interference caused by RNA coexisting with the recovered nucleic acid can be reduced. It is also preferred to add a deoxyribonuclease inhibitor. In the case of recovering a nucleic acid other than DNA, e.g., RNA, on the other hand, a deoxyribonuclease is preferably added to a nucleic acid solubilizing reagent solution. In this case, interference caused by DNA coexisting with the recovered nucleic acid can be reduced. It is also preferred to add a ribonuclease inhibitor. As the ribonuclease inhibitor, one capable of inhibiting specifically a ribonuclease is preferred. The ribonuclease is not particularly limited, and for example, a degradative enzyme capable of decomposing specifically RNA, such as ribonuclease H (RNase H), can be preferably used. The deoxyribonuclease is not particularly limited, and for example, a degradative enzyme capable of decomposing specifically DNA, such as DNase I, can be preferably used. The nuclease and the nuclease inhibitor can be used in concentrations that are ordinarily employed. A heating treatment may be carried out in the ordinary manner. The heating treatment is preferably carried out simultaneously with the treatment with a protease.

As the nucleic acid stabilizer, one can mention those having a function of deactivating the activity of a nuclease. Some kinds of analytes contain a nuclease decomposing a nucleic acid, and upon homogenizing a nucleic acid, the nuclease acts on the nucleic acid to drastically reduce the yield in some cases. The aforementioned nucleic acid stabilizer can allow stabilized presence of a nucleic acid in an analyte, whereby the recovered amount and the recovered efficiency of a nucleic acid are favorably improved to facilitate reduction of the necessary amount of the analyte and acceleration of the process speed.

As the nucleic acid stabilizer having a function of deactivating the activity of a nuclease, a compound that is generally used as a reducing agent can be used. As such a reducing agent, a hydrogenating compound such as hydrogen, hydrogen iodide, hydrogen sulfide, aluminum lithium hydride and boron sodium hydride, a metal having a large electo-positivity, such as an alkali metal, magnesium, calcium aluminum and zinc, amalgams of these metals, an aldehyde compound, a saccharide, an organic acid compound such as formic acid and oxalic acid, and a mercapto compound can be mentioned. Among these, a mercapto compound is preferred. As the mercapto compound, N-acetylcysteine, mercaptoethanol and alkylmercaptan can be mentioned. In particular, β-mercaptoethanol is preferred. The mercapto compound may be used solely or in combination of plural kinds thereof. The nucleic acid stabilizer is preferably used in the pretreating solution in a concentration of from 0.1 to 20% by mass, and more preferably from 0.3 to 15% by mass. The mercapto compound is preferably used in the pretreating solution in a concentration of from 0.1 to 10% by mass, and more preferably from 0.5 to 5% by mass.

In the step of dissolving a cell membrane and a nuclear membrane and solubilizing a nucleic acid to obtain a sample solution containing a nucleic acid from an analyte, the sample solution containing a nucleic acid preferably contains a defoaming agent. As the aforementioned defoaming agent, the two ingredients of a silicone defoaming agent and an alcoholic defoaming agent are preferably mentioned. As the alcoholic deforming agent, an acetylene glycol surfactant is preferred.

As specific examples of the defoaming agent, a silicone defoaming agent (such as a silicone oil, dimethylpolysiloxane, a silicone emulsion, modified polysiloxane and a silicone compound), an alcoholic defoaming agent (for example, acetylene glycol, heptanol, ethylhexanol, a higher alcohol and polyoxyalkylene glycol), an ether defoaming agent (for example, heptylcellosolve and nonylcellosolve-3-heptylcorbitol), a fat or oil defoaming agent (for example, animal and vegetable oils), a fatty acid defoaming agent (for example, stearic acid, oleic acid and palmitic acid), a metal soap defoaming agent (for example, aluminum stearate and calcium stearate), a fatty acid ester defoaming agent (for example, natural wax and tributyl phosphate), a phosphate ester defoaming agent (for example, sodium octylphosphate), an amine defoaming agent (for example, diamylamine), an amide defoaming agent (for example, stearic acid amide), and other defoaming agents (for example, ferric sulfate and bauxite) can be mentioned. Particularly preferably, the two ingredients of a silicone defoaming agent and an alcoholic defoaming agent can be used in combination. As the alcoholic defoaming agent, an acetylene glycol surfactant is also preferably used.

The nucleic acid solubilizing reagent is also preferably supplied in a dried state. A container that contains in advance a dried (for example, freeze-dried) protease may be employed. The sample solution containing a nucleic acid can be obtained by using both of vessels, one filled with the aforementioned nucleic acid solubilizing agent supplied in a dried state, and the other with a dried protease beforehand. In the case where the sample solution containing a nucleic acid is obtained in the aforementioned method, the nucleic acid solubilizing reagent and the protease enjoy improved storage stability, whereby the operation is simplified without changing the yield of a nucleic acid.

The method for mixing the analyte with the nucleic acid solubilizing reagent is not particularly limited. They are preferably mixed with a stirring device at a rate of from 30 to 3,000 rpm for a period of from 1 second to 3 minutes. According to the operation, the yield of a nucleic acid to be separated and purified can be increased. They are also preferably mixed by rollover mixing in 5 to 30 times. They may also be mixed by a pipetting operation in 10 to 50 times. In this case, the yield of a nucleic acid to be separated and purified can be increased by a simple operation.

In the case of using the nucleic acid solubilizing reagent solution containing a protease, a mixed solution of an analyte and the nucleic acid solubilizing reagent solution may be incubated at the optimal temperature and reaction time for the protease to increase the yield of a nucleic acid to be separated and purified. The incubation temperature is generally from 20 to 70° C., and preferably the optimal temperature for the protease. The incubation time is generally from 1 minute to 18 hours, and preferably the optimal time for the protease. The incubation, the method of which is not particularly limited, can be carried out by placing in a hot water bath or a heating vessel.

In the step of dissolving a cell membrane and a nuclear membrane and solubilizing a nucleic acid to obtain a sample solution containing a nucleic acid from an analyte, the water-soluble organic solvent added to the incubated mixture includes an alcohol, acetone, acetonitrile and dimethylformamide. In particular, an alcohol is preferably used.

The alcohol may be a primary alcohol, a secondary alcohol or a tertiary alcohol. Methyl alcohol, ethyl alcohol, propyl alcohol and an isomer thereof, and butyl alcohol and an isomer thereof can be preferably used. Ethanol can be more preferably used. The water-soluble organic solvent may be used solely or in combination of plural kinds thereof. The concentration of the water-soluble organic solvent in the nucleic acid solubilizing reagent solution is preferably from 1 to 20% by mass. The final concentration of the water-soluble organic solvent in the sample solution containing a nucleic acid is preferably from 5 to 90% by mass.

In the aforementioned step of dissolving a cell membrane and a nuclear membrane and solubilizing a nucleic acid to obtain a sample solution containing a nucleic acid from an analyte, the sample solution preferably has pH of from 5 to 10, more preferably pH of from 6 to 9, and further preferably pH of from 7 to 8.

In the aforementioned process for dissolving a cell membrane and a nuclear membrane and solubilizing a nucleic acid to obtain a sample solution containing a nucleic acid from an analyte, the resulting sample solution containing a nucleic acid preferably has a surface tension of 0.05 $J/m^2$ or less, a viscosity of from 1 to 10,000 mPa, and a specific gravity of from 0.8 to 1.2.

The rinsing step will be described below. The recovered amount and the purity of a nucleic acid are improved by rinsing, whereby the necessary amount of the analyte containing a nucleic acid can be reduced. The rinsing step may be completed only with a single operation of rinsing for speeding up the process, and in the case where the purity is a more important factor, the rinsing operation is preferably repeated in plural times.

In the rinsing step, a rinsing solution is supplied to the nucleic acid separation and purification cartridge having the nucleic acid-adsorbing porous membrane accommodated therein by using an automatic injecting device or a supplying means having a function equivalent thereto. The rinsing solution may be supplied from one opening of the nucleic acid separation and purification cartridge (i.e., the opening, from which the sample solution containing a nucleic acid is injected), and the interior of the nucleic acid separation and purification cartridge may be pressurized by using a pressure difference generating apparatus connected to the one opening to pass the rinsing solution through the nucleic acid-adsorbing porous membrane and to discharge from the other opening. Alternatively, the rinsing solution may be supplied from the one opening and then discharged from the same opening. Furthermore, the rinsing solution may be supplied from the other opening than the one opening, from which the sample solution containing a nucleic acid is injected, and then discharged from the same other opening. However, the method that the rinsing solution is supplied from one opening of the nucleic acid separation and purification cartridge, and then passed through the nucleic acid-adsorbing porous membrane and to discharge from the other opening than the one opening is preferred owing to the excellent rinsing efficiency obtained thereby. The amount of the rinsing solution in the rinsing step is preferably 2 $\mu L/mm^2$ or more. While a larger amount of the rinsing solution improves the rinsing efficiency, the amount is preferably 200 $\mu L/mm^2$ or less for maintaining the operability and for preventing the sample from flowing out.

The flow rate upon passing the rinsing solution through the nucleic acid-adsorbing porous membrane in the rinsing step is preferably from 2 to 1,500 $\mu L$/sec, and more preferably from 5 to 700 $\mu L$/sec, per unit area ($cm^2$) of the membrane. The rinsing operation can be sufficiently carried out by decreasing the flow rate to take a prolonged period of time, but the aforementioned range is preferably chosen since it is also important to speed up the separation and purification operation of a nucleic acid.

In the rinsing step, the temperature of the rinsing solution is preferably from 4 to 70° C., and is more preferably room temperature. In the rinsing step, the rinsing operation can be carried out while the nucleic acid separation and purification cartridge is subjected to agitation caused by mechanical vibration or ultrasonic wave application, or to centrifugal separation.

In the rinsing step, the rinsing solution generally does not contain an enzyme such as a nuclease, but may contain an enzyme that decomposes impurities such as protein. In some cases, a deoxyribonuclease or a ribonuclease may also be contained. By using a rinsing solution containing a deoxyribonuclease, only RNA can be selectively recovered from an analyte. By using a rinsing solution containing a ribonuclease, on the other hand, only DNA can be selectively recovered from an analyte.

In the rinsing step, the rinsing solution is preferably a solution containing a water-soluble organic solvent and/or a water-soluble salt. The rinsing solution must have a function of rinsing out impurities in the sample solution that are adsorbed in the nucleic acid-adsorbing porous membrane together with a nucleic acid. In order to attain the function, it is necessary that the rinsing solution has such a composition that, though a nucleic acid is not desorbed from the nucleic acid-adsorbing porous membrane, the impurities are desorbed therefrom. For the purpose, a water-soluble organic solvent such as an alcohol is suitable for desorbing the other components than a nucleic acid because a nucleic acid has poor solubility in the water-soluble organic solvent. Moreover, since the addition of a water-soluble salt improves the adsorption efficiency of a nucleic acid, the function of selective removal of the unnecessary components is enhanced.

As the example of the water-soluble organic solvent contained in the rinsing solution, methanol, ethanol, isopropanol, n-propanol, butanol and acetone can be used, and among these, ethanol is preferably used. The amount of the water-soluble organic solvent contained in the rinsing solution is preferably from 20 to 100% by weight, and more preferably from 40 to 80% by weight.

On the other hand, the water-soluble salt contained in the rinsing solution is preferably a salt of a halide, among which a chloride is more preferred. The water-soluble salt is preferably a monovalent or divalent cation, and more preferably, an alkali metal salt or an alkaline earth metal salt, with a sodium salt and potassium salt being particularly preferred among them. In the case where the water-soluble salt is contained in the rinsing solution, the concentration thereof is preferably 10 mmole/L or more, and the upper limit thereof is not particularly limited as far as the solubility of impurities is not impaired, and is preferably 1 mole/L or less, and more preferably 0.1 mole/L or less. It is particularly preferred that the water-soluble salt is sodium chloride, and that sodium chloride is contained in a concentration of 20 mmole/L or more.

The rinsing solution preferably does not contain chaotropic substance, whereby such a possibility can be reduced that a chaotropic substance is mixed therein in the recovering step subsequent to the rinsing step. In the case where a chaotropic substance is mixed in the recovering step, the enzyme reaction, such as PCR, is often impaired, and therefore, it is ideal that the rinsing solution contains no chaotropic substance in consideration of subsequent enzyme reactions. In addition, since a chaotropic substance is corrosive and harmful, the disuse of a chaotropic substance is significantly advantageous for the operator from the viewpoint of the safety in experimental operation. The chaotropic substance referred herein includes urea, a guanidine salt, sodium isothiocyanate, sodium iodide and potassium iodide, as described hereinabove.

In a rinsing step during the process of separation and purification of a nucleic acid according to the conventional technique, a rinsing solution often remains in a vessel such as a cartridge, since the rinsing solution has high wettability to the vessel and the rinsing solution is contaminated into the recovering step succeeding the rinsing step to cause reduction in the purity of a nucleic acid and the lowering in reactivity in the subsequent step. Therefore, in the case where a vessel such as a cartridge is used for the adsorption and desorption of a nucleic acid, it is important that the solution used for rinsing, particularly a rinsing solution, is prevented from remaining in the cartridge to avoid adverse affect on the subsequent step.

Accordingly, in order to prevent the rinsing solution in the rinsing step from contamination in the recovering solution for the subsequent step to minimize the amount of the rinsing solution remaining in the cartridge, the rinsing solution preferably has a surface tension of less than $0.035$ $J/m^2$. The reduction in surface tension improves the wettability between the rinsing solution and the cartridge to suppress the amount of the remaining solution.

Inversely, it is also possible that for the purpose of reducing the remaining amount of the rinsing solution used in the rinsing step, the surface tension of the rinsing solution is made $0.035$ $J/m^2$ or more to facilitate running off of droplets of the rinsing solution by forming droplets due to enhanced water-repellency to the cartridge wall, whereby the amount of the solution remaining is reduced. Either of such surface tensions can be chosen depending on the combination of the porous membrane having a nucleic acid adsorbed therein, the recovering solution and the rinsing solution.

The rinsing step can be simplified by using the nucleic acid-adsorbing porous membrane of the invention, i.e., (1) it is sufficient that the rinsing solution is passed through the nucleic acid-adsorbing porous membrane only once, (2) the rinsing step can be carried out at room temperature, (3) the recovering solution can be injected to the cartridge immediately after rinsing, and (4) one, or two or more of the advantages (1), (2) and (3) can be conducted. This is because the drying step can be omitted in the invention since the nucleic acid-adsorbing porous membrane of the invention is in a form of a thin membrane, while, in the conventional technique, a drying step is often necessary for rapid removal of the organic solvent contained in a rinsing solution.

There has been a problem that in the rinsing step of the process of separation and purification of a nucleic acid, a rinsing solution is scattered and attached to external portions to contaminate a sample. The contamination of this kind in the rinsing step can be suppressed by modifying the shapes of the nucleic acid separation and purification cartridge having the nucleic acid-adsorbing porous membrane accommodated in the vessel having two openings and of the waste liquor container.

A step of recovering a nucleic acid by desorbing from the nucleic acid-adsorbing porous membrane will be described below. In the recovering step, a recovering solution is supplied to the cartridge for separation and purification of a nucleic acid having the nucleic acid-adsorbing porous membrane accommodated therein by using an automatic injecting device or a supplying means having a function equivalent thereto. The recovering solution may be supplied from one opening of the cartridge for separation and purification of a nucleic acid (i.e., the opening, from which the sample solution containing a nucleic acid is injected), and the interior of the nucleic acid separation and purification cartridge may be pressurized by using a pressure difference generating apparatus connected to the one opening to pass the recovering solution through the nucleic acid-adsorbing porous membrane and to discharge the solution from the other opening. Alternatively, the recovering solution may be supplied from the one opening and then discharged from the same opening. Furthermore, the recovering solution may be supplied from the other opening than the one opening, from which the sample solution containing a nucleic acid is injected, and then discharged from the same other opening. However, It is preferred to employ the method of supplying the recovering solution from one opening of the nucleic acid separation and purification cartridge, and then passing the solution through the nucleic acid-adsorbing porous membrane and to discharge the solution from the other opening than the one opening owing to excellent recovering efficiency obtained thereby.

The desorption of a nucleic acid can be carried out by adjusting the volume of the recovering solution with respect to the volume of the sample solution containing the nucleic acid prepared from an analyte. The amount of the recovering solution containing the nucleic acid thus separated and purified depends on the amount of the analyte used. The amount of the recovering solution that is ordinarily employed is from several tens to several hundreds μL, and in the opposite case where the amount of the analyte is considerably small, or in the case where a large amount of a nucleic acid is to be separated and purified, the amount of the recovering solution may vary from 1 μL to several tens mL.

As the preferred example of the recovering solution, distilled water and a Tris/EDTA buffer can be used. In the case where a nucleic acid thus recovered is subjected to PCR (polymerase chain reaction), a buffer solution used in the PCR (for example, an aqueous solution having final concentrations of KCl 50 mmole/L, Tris-CL 10 mmole/L and $MgCl_2$ 1.5 mmole/L) may be used.

The recovering solution preferably has pH of from 2 to 11, and more preferably pH of from 5 to 9. In particular, the ionic strength and the salt concentration thereof influence on elution of the adsorbed nucleic acid. The recovering solution preferably has an ionic strength of 290 mmole/L or less and a salt concentration of 90 mmole/L or less. According to the constitution, the recovering rate of a nucleic acid is improved to recover a larger amount of a nucleic acid. The nucleic acid to be recovered may be of single-strand or duplex.

By reducing the volume of the recovering solution in comparison to that of the initial sample solution containing a nucleic acid, the recovering solution containing the nucleic acid in a raised concentration can be obtained. The ratio of the volume of the recovering solution to the volume of the sample solution (recovering solution/sample solution) can be preferably adjusted to 1/100 to 99/100, and more preferably from 1/10 to 9/10. With such a measure, the nucleic acid can be easily concentrated without any operation for concentrating the nucleic acid in the process for separation and purification of the nucleic acid. A method of providing a nucleic acid solution containing a nucleic acid in an increased concentration can be provided in the aforementioned manner.

As another method, it is possible that a nucleic acid is desorbed with the recovering solution of a larger amount than that of the initial sample solution containing the nucleic acid to obtain the recovering solution having a desired concentration of the nucleic acid, thus the recovering solution containing the nucleic acid in such a concentration suitable for the subsequent step (such as PCR). The ratio of the volume of the recovering solution to the volume of the sample solution (recovering solution/sample solution) is preferably from 1/1 to 50/1, and more preferably from 1/1 to 5/1. With such a measure, the operation can be simplified by omitting the step of adjusting the concentration after separating and purifying the nucleic acid. Furthermore, by using a sufficiently large amount of the recovering solution, the recovering rate of the nucleic acid from the porous membrane can be improved.

The number of the injection operation of the recovering solution is not particularly limited, and may be only one time or plural times. In general, when a nucleic acid is to be separated and purified in a rapid and simple manner, the recovering operation may be carried out in one time, and when a large amount of a nucleic acid is to be recovered, the recovering solution may be injected in plural times.

In the recovering step, the recovering solution for a nucleic acid may have such a composition that can be used in the subsequent step. A nucleic acid thus separated and purified is often amplified by the PCR (polymerase chain reaction) method. In this case, it is necessary that the nucleic acid solution thus separated and purified is diluted with a buffer solution suitable for the PCR method. By using a buffer solution suitable for the PCR method in the recovering step of the process herein, the operation can be transferred to the subsequent PCR method easily and rapidly.

In the recovering step, the recovering solution may contain a stabilizer for preventing the recovered nucleic acid from decomposition. As the stabilizer, an antibacterial agent, antifungal agent and a nucleic acid decomposition inhibitor can be added. As the nucleic acid decomposition inhibitor, EDTA can be mentioned. Further, as another embodiment, the stabilizer may be added to the recovering container in advance.

The recovering container used in the recovering step is not particularly limited, and a recovering container produced with a material having no absorption at the wavelength of 260 nm can be used. In this case, the concentration of the recovered nucleic acid solution can be measured without transfer to another container. Examples of the material having no absorption at 260 nm wavelength include quartz glass, but the invention is not limited thereto.

According to the invention, a cartridge retaining mechanism equipped in a nucleic acid extracting apparatus capable of maintaining airtightness during pressurized air feeding can be provided without practicing any drastic modification on the constitution of the nucleic acid extracting apparatus.

The entire disclosure of each and every foreign patent application from which the benefit of foreign priority has been claimed in the present application is incorporated herein by reference, as if fully set forth.

What is claimed is:

1. A cartridge retaining mechanism equipped in a nucleic acid extracting apparatus for extracting a nucleic acid, the cartridge retaining mechanism comprising:
   a cartridge that comprises:
      a cartridge main body that has a cylindrical shape with a bottom, and the bottom is shaped in a funnel shape;
      a nucleic acid-adsorbing solid carrier that traps a nucleic acid, and the nucleic acid-adsorbing solid carrier is disposed at the bottom of the cartridge main body; and
      a cartridge cap that is detachably mounted on an open end of the cartridge main body,
   a supporting part that supports the cartridge; and
   a pressure-proof retaining part that pushes the cartridge cap,
   wherein a cylindrical rib with a diameter smaller than a diameter of the cartridge main body is formed on an upper plane of the cartridge cap so that the cylindrical rib protrudes from the upper plane;
   a nozzle-receiving opening to which a pressure nozzle is pressed is formed at the cylindrical rib; and
   an aperture through which the cylindrical rib is inserted is formed in the pressure-proof retaining part, and
   wherein when the pressure nozzle is pressed to the nozzle-receiving opening, along with the nozzle-receiving opening being exposed from the aperture, the cartridge cap is pressed by the pressure-proof retaining part and simultaneously the cartridge main body is supported by the supporting part.

2. The cartridge retaining mechanism according to claim 1, wherein the cartridge cap has a configuration to be fitted to the cartridge main body.

3. The cartridge retaining mechanism according to claim 2, wherein the cartridge cap has a fitting protrusion and the cartridge main body has a fitting groove.

4. The cartridge retaining mechanism according to claim 2, wherein the cartridge cap has a fitting groove and the cartridge main body has a fitting protrusion.

* * * * *